(12) United States Patent
Gerber et al.

(10) Patent No.: US 7,706,889 B2
(45) Date of Patent: Apr. 27, 2010

(54) TREE-BASED ELECTRICAL STIMULATOR PROGRAMMING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 217 days.

(21) Appl. No.: 11/799,113

(22) Filed: Apr. 30, 2007

(65) Prior Publication Data

US 2007/0265664 A1 Nov. 15, 2007

Related U.S. Application Data

(63) Continuation-in-part of application No. 11/414,527, filed on Apr. 28, 2006.

(51) Int. Cl.
*A61N 1/36* (2006.01)
(52) U.S. Cl. ............................................. 607/59; 607/2
(58) Field of Classification Search ...................... 607/2, 607/54
See application file for complete search history.

(56) References Cited

U.S. PATENT DOCUMENTS

| | | | |
|---|---|---|---|
| 4,236,524 A | 12/1980 | Powell et al. |
| 4,872,122 A | 10/1989 | Altschuler et al. |
| 4,895,574 A | 1/1990 | Rosenberg |
| 5,005,143 A | 4/1991 | Altschuler et al. |
| 5,240,009 A | 8/1993 | Williams |
| 5,280,792 A | 1/1994 | Leong et al. |
| 5,358,513 A | 10/1994 | Powell, III et al. |
| 5,383,910 A | 1/1995 | den Dulk |

(Continued)

FOREIGN PATENT DOCUMENTS

EP  0 541 338 B1  5/1993

(Continued)

OTHER PUBLICATIONS

"Notice of Transmittal of the International Search Report and the Written Opinion of the International Searching Authority, or the Declaration," dated Jan. 16, 2008 for corresponding PCT Application No. PCT/US2007/01398, (12 pgs.).

(Continued)

*Primary Examiner*—Carl H Layno
*Assistant Examiner*—Jeremiah T Kimball
(74) *Attorney, Agent, or Firm*—Shumaker & Sieffert, P.A.

(57) ABSTRACT

The disclosure describes an implantable stimulation system that guides programming with a therapeutic tree. All possible stimulation parameters are arranged on the therapeutic tree, with each level of the therapeutic tree containing a different stimulation parameter type. Each level includes nodes that are connected to nodes of adjacent levels. A program path is created by moving through nodes of lower levels. The stimulation parameter types are arranged so that coarse adjustments occur at higher levels of the tree and fine adjustments occur at lower levels of the tree. The nodes of the program path define the stimulation parameters of the delivered stimulation therapy. Performance feedback may be used by the system to evaluate nodes of the therapeutic tree and define the program path. The performance feedback may include beneficial effects, adverse effects, and system performance related to the stimulation therapy. Additionally, one or more sensors may provide the performance feedback.

43 Claims, 17 Drawing Sheets

U.S. PATENT DOCUMENTS

| | | |
|---|---|---|
| 5,443,486 A | 8/1995 | Hrdlicka et al. |
| 5,522,863 A | 6/1996 | Spano et al. |
| 5,626,140 A | 5/1997 | Feldman et al. |
| 5,645,069 A | 7/1997 | Lee |
| 5,673,367 A | 9/1997 | Buckley |
| 5,702,429 A | 12/1997 | King |
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |
| 5,782,885 A | 7/1998 | Andersson |
| 5,810,014 A | 9/1998 | Davis et al. |
| 5,867,386 A | 2/1999 | Hoffberg et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,995,868 A | 11/1999 | Dorfmeister et al. |
| 5,999,854 A | 12/1999 | Deno et al. |
| 6,038,476 A | 3/2000 | Schwartz |
| 6,081,750 A | 6/2000 | Hoffberg et al. |
| 6,129,745 A | 10/2000 | Sun et al. |
| 6,171,239 B1 | 1/2001 | Humphrey |
| 6,192,273 B1 | 2/2001 | Igel et al. |
| 6,263,230 B1 | 7/2001 | Haynor et al. |
| 6,269,267 B1 | 7/2001 | Bardy et al. |
| 6,308,102 B1 | 10/2001 | Sieracki et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,249 B1 | 3/2003 | Kadhiresan et al. |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,609,032 B1 * | 8/2003 | Woods et al. ............ 607/46 |
| 6,612,983 B1 | 9/2003 | Marchal |
| 6,658,287 B1 | 12/2003 | Litt et al. |
| 6,659,968 B1 | 12/2003 | McClure |
| 6,662,051 B1 | 12/2003 | Eraker et al. |
| 6,687,538 B1 | 2/2004 | Hrdlicka et al. |
| 6,697,672 B2 | 2/2004 | Andersson |
| 6,704,595 B2 | 3/2004 | Bardy |
| 7,050,856 B2 | 5/2006 | Stypulkowski |
| 7,123,961 B1 * | 10/2006 | Kroll et al. ............ 607/9 |
| 7,142,923 B2 | 11/2006 | North et al. |
| 7,415,308 B2 * | 8/2008 | Gerber et al. ............ 607/41 |
| 2002/0016699 A1 | 2/2002 | Hoggart et al. |
| 2002/0038294 A1 | 3/2002 | Matsugu |
| 2002/0045804 A1 | 4/2002 | Christopherson et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0103512 A1 | 8/2002 | Echauz et al. |
| 2002/0123673 A1 | 9/2002 | Webb et al. |
| 2002/0138013 A1 | 9/2002 | Guerrero et al. |
| 2002/0151992 A1 | 10/2002 | Hoffberg et al. |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0135248 A1 | 7/2003 | Stypulkowski |
| 2003/0158587 A1 | 8/2003 | Esteller et al. |
| 2003/0195569 A1 | 10/2003 | Swerdlow et al. |
| 2003/0216620 A1 | 11/2003 | Jain et al. |
| 2003/0216654 A1 | 11/2003 | Xu et al. |
| 2004/0103001 A1 | 5/2004 | Mazar et al. |
| 2004/0129271 A1 | 7/2004 | Hickle |
| 2004/0143302 A1 | 7/2004 | Sieracki et al. |
| 2004/0199217 A1 | 10/2004 | Lee et al. |
| 2004/0215288 A1 | 10/2004 | Lee et al. |
| 2004/0267330 A1 | 12/2004 | Lee et al. |
| 2005/0043774 A1 | 2/2005 | Devlin et al. |
| 2005/0060007 A1 * | 3/2005 | Goetz ............ 607/48 |
| 2005/0060008 A1 | 3/2005 | Goetz |
| 2005/0060009 A1 | 3/2005 | Goetz |
| 2005/0060010 A1 | 3/2005 | Goetz |
| 2005/0075669 A1 | 4/2005 | King |
| 2005/0080462 A1 | 4/2005 | Jenkins et al. |
| 2005/0177206 A1 | 8/2005 | North et al. |
| 2005/0209644 A1 * | 9/2005 | Heruth et al. ............ 607/3 |
| 2005/0222643 A1 | 10/2005 | Heruth et al. |
| 2005/0245988 A1 | 11/2005 | Miesel |
| 2006/0020292 A1 | 1/2006 | Goetz et al. |
| 2006/0190047 A1 | 8/2006 | Gerber et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0190061 A1 | 8/2006 | Stypulkowski |
| 2006/0195145 A1 | 8/2006 | Lee et al. |
| 2006/0206162 A1 | 9/2006 | Wahlstrand et al. |
| 2006/0206163 A1 | 9/2006 | Wahlstrand et al. |
| 2006/0235472 A1 | 10/2006 | Goetz et al. |
| 2006/0259099 A1 * | 11/2006 | Goetz et al. ............ 607/66 |
| 2006/0270944 A1 | 11/2006 | King |

FOREIGN PATENT DOCUMENTS

| | | |
|---|---|---|
| EP | 0 653 224 A2 | 5/1995 |
| EP | 0 653 224 BI | 5/1995 |
| EP | 0 684 858 B1 | 12/1995 |
| EP | 0 756 877 A2 | 2/1997 |
| EP | 0 796 636 A1 | 9/1997 |
| EP | 0 848 965 A2 | 6/1998 |
| EP | 0 848 965 B1 | 6/1998 |
| EP | 0 882 469 B1 | 12/1998 |
| EP | 1 192 971 B1 | 4/2002 |
| WO | WO 00/10455 A1 | 3/2000 |
| WO | WO 01/17419 A1 | 3/2001 |
| WO | WO 01/43823 A1 | 6/2001 |
| WO | WO 01/47600 A1 | 7/2001 |
| WO | WO 01/56467 A1 | 8/2001 |
| WO | WO 01/60445 A2 | 8/2001 |
| WO | WO 01/82995 A3 | 11/2001 |
| WO | WO 02/02622 A2 | 1/2002 |
| WO | WO 02/15777 A1 | 2/2002 |
| WO | WO 03/043690 A1 | 5/2003 |
| WO | WO 03/051175 A2 | 6/2003 |
| WO | WO 03/094721 A1 | 11/2003 |

| | | |
|---|---|---|
| WO | WO 2004/041352 A1 | 5/2004 |
| WO | WO 2004/075982 A1 | 9/2004 |
| WO | WO 2004/096349 A1 | 11/2004 |
| WO | WO 2004/096358 A2 | 11/2004 |
| WO | WO 2005/028028 A1 | 3/2005 |
| WO | WO 2005/039688 A2 | 5/2005 |
| WO | WO 2005/089648 A1 | 9/2005 |
| WO | WO 2006/012423 A1 | 2/2006 |
| WO | WO2006/098823 A1 | 9/2006 |
| WO | WO2006/098824 A1 | 9/2006 |

OTHER PUBLICATIONS

U.S. Appl. No. 11/799,114, filed Apr. 30, 2007, entitled "Tree-Based Electrical Stimulator Programming for Pain," by Gerber et al.

U.S. Appl. No. 11/414,527, filed Apr. 28, 2006, entitled "Tree-Based Electrical Stimulator Programming", by Rondoni et al.

"Notification Concerning Transmittal of International Preliminary Report on Patentability," dated Nov. 6, 2008 for corresponding PCT Application No. PCT/US2007/010398, (8 pgs.).

Office Action dated Dec. 31, 2008 for U.S. Appl. No. 11/414,527 (12 pgs.).

Responsive Amendment dated Mar. 31, 2009 for U.S. Appl. No. 11/414,527 (18 pgs.).

Office Action dated Dec. 31, 2008 for U.S. Appl. No. 11/799,114 (14 pgs.).

Responsive Amendment dated Mar. 31, 2009 for U.S. Appl. No. 11/799.114 (17 pgs.).

Office Action dated Jul. 13, 2009 for U.S. Appl. No. 11/799,114 (14 pgs.).

Responsive Amendment dated Sep. 14, 2009 for U.S. Appl. No. 11/799,114 (17 pgs.).

Advisory Action dated Sep. 24, 2009 for U.S. Appl. No. 11/799,114 (3 pgs.).

Office Action dated Sep. 2, 2009 for U.S. Appl. No. 11/414,527 (12 pgs.).

Response dated Nov. 2, 2009 for U.S. Appl. No. 11/414,527 (7 pgs.).

* cited by examiner

FIG. 16A  FIG. 16B

TREE-BASED ELECTRICAL STIMULATOR PROGRAMMING

This application is a continuation-in-part of U.S. application Ser. No. 11/414,527, filed Apr. 28, 2006, the entire content of which is incorporated herein by reference.

TECHNICAL FIELD

The invention relates to medical devices and, more particularly, electrical stimulators.

BACKGROUND

Electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target locations associated with the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width, and a pulse rate for stimulation pulses to be delivered to the patient. A group of parameters, including electrode configuration (electrode combination and electrode polarity), amplitude, pulse width and pulse rate, may be referred to as a program in the sense that they drive the neurostimulation therapy to be delivered to the patient.

The process of selecting stimulation parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician may test stimulation parameters by manually specifying parameters based on intuition or some idiosyncratic methodology. The clinician may then record notes on the efficacy and side effects of each parameter set after delivery of stimulation via that combination. Upon receipt of patient feedback and/or observation of symptoms by the clinician, the clinician is able to compare and select from the tested programs.

SUMMARY

The disclosure describes an implantable stimulation system that guides programming with a therapeutic tree. A number of possible stimulation parameters are arranged on the therapeutic tree, with each level of the therapeutic tree containing a different stimulation parameter type. Each level includes nodes that are connected to nodes of adjacent levels. A program path is created by moving through nodes of lower levels. The stimulation parameter types are arranged so that coarse adjustments occur at higher levels of the tree and fine adjustments occur at lower levels of the tree. The nodes of the program path define the stimulation parameters of the delivered stimulation therapy. Performance feedback may be used by the system to evaluate nodes of the therapeutic tree and define the program path. The performance feedback may include beneficial effects, adverse effects, and system performance related to the stimulation therapy. Additionally, one or more sensors may provide the performance feedback.

Electrical stimulation therapy is generally defined by a group of parameters, including electrode combination, electrode polarity, current or voltage amplitude, stimulation pulse width, and stimulation pulse rate. A variety of stimulation parameters are associated with the nodes in the therapeutic tree. In particular, each level of the therapeutic tree contains nodes representing adjustment of a different type of stimulation parameter.

The stimulation parameter types may be arranged so that higher priority adjustments occur at higher levels of the tree and lower priority adjustments occur at lower levels of the tree. In particular, the parameters are prioritized so that parameters believed to have the largest impact on performance feedback are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

The nodes of the program path define the stimulation parameters of the delivered stimulation therapy. A clinician, patient, or device traverses the levels and nodes of the tree based on performance feedback from the patient, objective observations by the clinician, and/or sensed physiological conditions indicative of performance of the stimulation therapy, e.g., beneficial effects, adverse effects, and system performance. The performance feedback permits navigation of an efficacious program path, resulting in a set of stimulation parameter values that support therapeutic efficacy.

If a selected node of the tree produces a therapeutic feedback improvement that exceeds a threshold level, then programming proceeds down the tree to the next level of nodes connected to the selected node. If the selected node does not produce a feedback improvement above the threshold level, then programming proceeds to other nodes at the same level of the tree as the selected node. The threshold level may be a subjective pain level based upon normal pain perceived by the patient without therapy.

For example, if a selected node corresponding to a particular pulse rate change is evaluated and found to yield a sufficient improvement, the process proceeds to nodes at the next level of the tree, which may represent adjustments to a pulse width value. While adjustments to pulse width are evaluated, the pulse rate value specified by the node in the upper level is maintained. Eventually, when a suitable pulse width value improvement is found, the process may proceed to nodes in the next level of the tree to evaluate amplitude adjustments. In this case, the pulse rate and pulse width are held constant according to the selected nodes in the upper levels of the tree while different amplitudes are evaluated.

A therapeutic tree, in accordance with this disclosure, may guide a clinician, a patient, a stimulator, or a programming device to programs containing effective parameters. A stimulator, for example, may communicate with an external programmer that receives patient or clinician input. The stimulator may also communicate with one or more sensors that measure a physiological parameter of the patient via a wired or wireless connection. The sensor may provide objective feedback or feedback input. When feedback input from the patient, clinician, or sensor indicates the improved or worsened pain therapy, the external programmer or stimulator may automatically traverse the therapeutic tree to modify the program for improved efficacy, reduction of side effects, or improved performance of the stimulator, e.g., reduced power consumption. In addition, the patient may input the dosage and frequency of pain medication taken to indicate how well the stimulation therapy is treating the patient's symptoms. Hence, the therapeutic tree may be used in initial programming of the stimulator by a clinician or patient, and/or during normal operation by the stimulator.

In one embodiment, the disclosure provides a method including defining a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify adjustment of different parameters. The method also includes defining a program path through the tree structure along a series of the interconnected nodes for which performance feedback regarding stimulation therapy delivered according to the stimulation parameters defined by the nodes exceeds a threshold level. In addition, the method includes selecting one of the nodes in the program path and delivering the stimulation therapy to a patient based on the parameters defined by the selected node to treat a patient.

In another embodiment, the disclosure provides a system that includes a memory defining a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify the adjustment of different parameters. The system also includes a processor that defines a program path through the tree structure along a series of the interconnected nodes for which performance feedback regarding stimulation therapy delivered according to the stimulation parameters defined by the nodes exceeds a threshold level, selects one of the nodes in the program path, and controls delivery of the stimulation therapy to a patient based on the parameters defined by the selected node to treat a patient.

In an additional embodiment, the disclosure provides a computer-readable medium including instructions that cause a processor to define a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify adjustment of different parameters. The instructions also cause a processor to define a program path through the tree structure along a series of the interconnected nodes for which performance feedback regarding stimulation therapy delivered according to the stimulation parameters defined by the nodes exceeds a threshold level. In addition, the instructions cause the processor to select one of the nodes in the program path and deliver the stimulation therapy to a patient based on the parameters defined by the selected node to treat a patient.

In various embodiments, the invention may provide one or more advantages. For example, the therapeutic tree provides a method to guide a user to find improved stimulation therapy based upon performance feedback from a clinician, the patient, a sensor, or the processor. The performance feedback may include beneficial effects and/or adverse effects caused by the therapy. In addition, the performance feedback may include system performance, so that the user may select a program path that minimizes power consumption, as an example. The performance feedback may be weighted during traversal of the therapeutic tree to define a program path such that, for example, side effects treated as being of more importance than efficacy, or a particular side effect is treated as being more important than other side effects. In this manner, the patient may benefit by achieving better stimulation therapy than would be found using trial and error or other stimulation parameter search mechanisms, or by achieving acceptable stimulation therapy more quickly.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
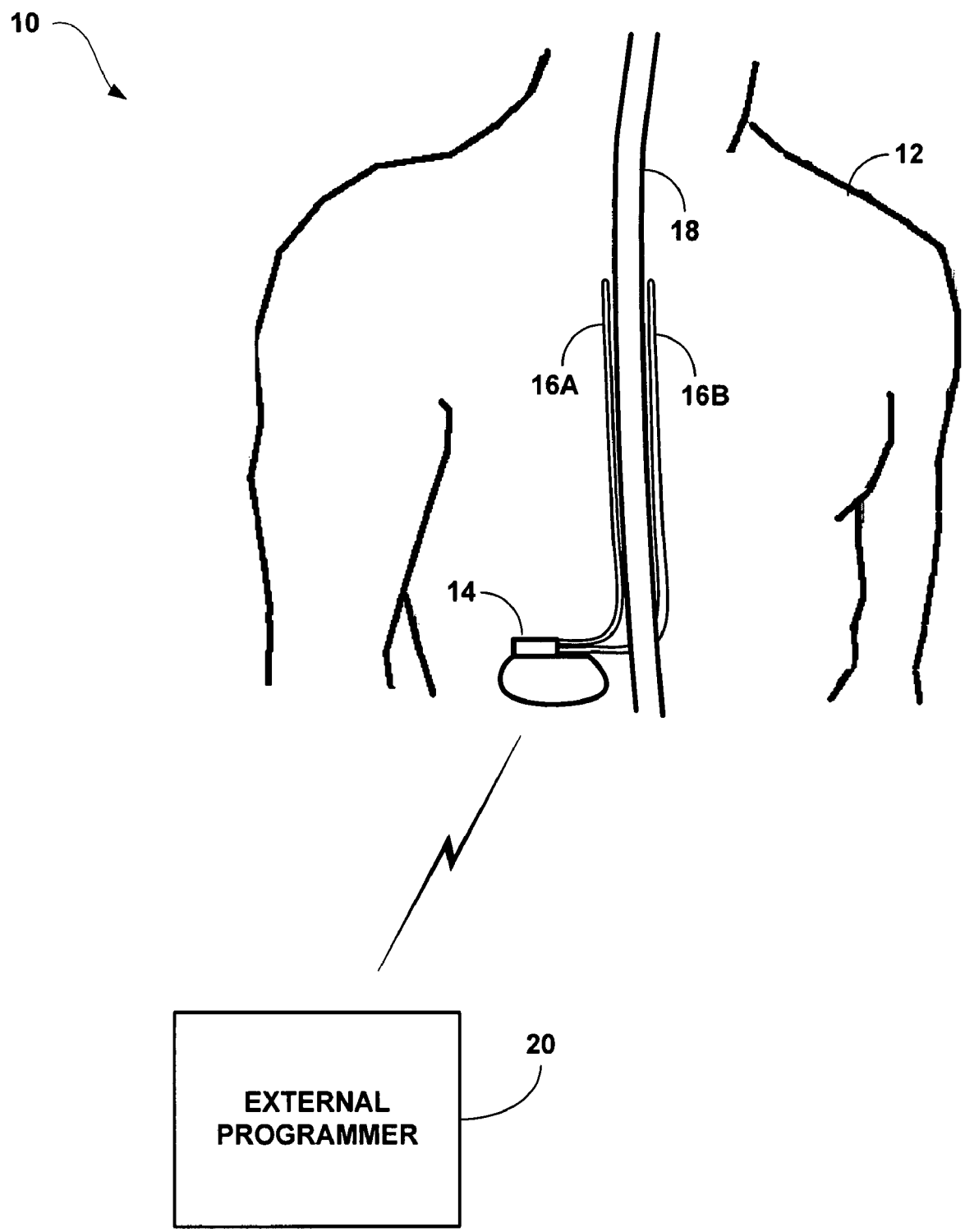
FIG. 1 is a schematic diagram illustrating an implantable spinal cord stimulation system in which stimulation is programmed based upon a therapeutic tree.

The disclosure is directed to techniques for guiding the programming of an electrical stimulator using a therapeutic tree and performance feedback. The techniques may be applicable to a variety of different electrical stimulators, including implantable electrical stimulators configured to deliver electrical stimulation therapy to patients to treat a variety of symptoms or conditions such as chronic pain, temporary pain, movement disorders, psychological disorders, or any other condition treated with electrical stimulation.

The stimulator may deliver neurostimulation therapy via one or more leads that include electrodes located proximate to target locations associated with the brain, central nervous system, spinal cord, peripheral nerves, or any other nerves associated with the condition of the patient. Stimulation may be used in different therapeutic applications, such as spinal cord stimulation (SCS), deep brain stimulation (DBS), cortical stimulation (CS), peripheral nerve stimulation (PNS), and peripheral nerve field stimulation (PNFS). In general, PNFS may be similar to PNS. However, for PNFS, the stimulation is generally not directed to any particular peripheral nerve, and is instead delivered generally to the area in which the patient experiences pain.

In this disclosure, for purposes of illustration, the techniques for guiding programming will be described in the context of electrical stimulation therapy for pain management therapy and deep brain stimulation therapy. Both SCS and DBS are described in the context of guiding programming using a therapeutic tree, but other therapies may also be treated accordingly.

Chronic pain may be a debilitating condition for a patient. Pain may prevent the patient from performing certain activities, interacting with other people in social situations, or even sleeping regularly. Chronic pain may be the result of injury, disease, age, or other conditions. Pain may originate at organs, muscles, nerves, or other tissues, and most pain signals are transferred though the spinal cord. Electrical stimulation of certain nerves, nerve plexuses, or the spinal cord may provide an effective therapy for pain experienced by the patient. Stimulation of the brain may also be effective for alleviating pain, such as neuropathic or nociceptive pain.

Movement disorders stemming from neurological dysfunction in the brain may also negatively affect the quality of life of a patient. Movement disorders may be the result of disease, age, injury, or other change causing mechanisms. Example movement disorders may include Parkinson's disease, tremor, multiple sclerosis, or spasticity. Furthermore, as used herein, the term "movement disorder" is also used to refer to epilepsy, and any other disorder which may result in irregular or otherwise symptomatic movement or non-movement. Electrical stimulation of neurons within the brain of the patient, e.g., DBS or CS, may reduce symptoms of movement disorders to improve the quality of life of the patient. In some cases, stimulation therapy may allow the patient to regain relatively normal control of their movements necessary to function independently.

In some embodiments of the invention, an implantable electrical stimulator may be provided. In some cases, electrical stimulation may permanently reduce symptoms. However, in other cases, stimulation with the same stimulation parameter set may become less efficacious through time due to accommodation. The electrical stimulator may be a stimulator that delivers electrical stimulation, to, for example, a portion of the spinal cord to block pain signals being transferred to the brain of the patient.

An electrical stimulator may be capable of thousands of different stimulation parameter sets, or programs that define the stimulation therapy. Providing a method to program the stimulation therapy to achieve the most efficacious therapy is important to patient health and quality of life. Without an effective tool to guide a user through selecting each stimulation parameter, the patient may not benefit from an optimal therapy program. In addition, the patient may not be able to effectively modify the stimulation program during chronic therapy.

A therapeutic tree, in accordance with this disclosure, guides a user, such as a patient or physician, to create a program path when setting initial chronic stimulation parameters or modifying current stimulation programs. Stimulation parameter types, such as electrode configuration, pulse rate, pulse width, and voltage amplitude, are arranged in the therapeutic tree so that the program path that connects multiple nodes of the tree defines the stimulation.

Performance feedback from the patient or clinician, or a sensor, may be used to create a program path that provides efficacious therapy for the patient. For example, if the performance feedback of stimulation delivered according to parameters associated with a selected node in the tree is increased by more than a threshold level, e.g., 50%, relative to the patient's baseline condition, the therapeutic tree will guide the user downward to nodes at the next level connected to the effective node. In this manner, the set of parameters can be refined to pursue further improvements. Efficacy may be a type of performance feedback. Other types of performance feedback include beneficial effects, adverse effects, and system performance. These feedback types may drive the selection of nodes to create the program path for therapy.

Alternatively, if the feedback does not exceed the threshold, the therapeutic tree may guide the user up the tree to evaluate different nodes at the same level as the selected node. The structure of the therapeutic tree and performance feedback may combine to decrease programming time and improve stimulation therapy efficacy, which may effectively improve patient quality of life.

In this disclosure, a therapeutic tree structure and a variety of performance feedback media, including patient input, clinician input, pain medication taken, sensor-based feedback, and processor calculated feedback are described for purposes of illustration. The feedback may include multiple inputs that the system uses in determining the efficacy of the stimulation pain therapy. For example, increased medication taken by the patient may indicate that stimulation therapy is not effective at controlling the patient's pain. However, the particular feedback implementations are merely for purposes of example, and should not be considered limiting of the invention as broadly embodied and described in this disclosure.

FIG. 1 is a schematic diagram illustrating an implantable spinal cord stimulation (SCS) system in which stimulation is programmed based upon a therapeutic tree. As shown in FIG. 1, system 10 includes implantable stimulator 14 and external programmer 20 shown in conjunction with a patient 12. Stimulation pulses are delivered to spinal cord 18 of patient 12 via one or more electrodes of leads 16A and 16B (collectively "leads 16"), where the electrode is placed adjacent to the target tissue of the spinal cord. In the example of FIG. 1, stimulation pulses are delivered to the spinal cord 18 to reduce the amount of pain perceived by patient 12. As mentioned above, however, the stimulator may be used with a variety of different pain therapies, such as peripheral nerve stimulation (PNS), peripheral nerve field stimulation (PNFS), deep brain stimulation (DBS), cortical stimulation (CS), and the like.

With reference to FIG. 1, a user, such as a clinician or patient 12, may interact with a user interface of external programmer 20 to provide system 10 with feedback indicating the efficacy and/or side effects of the stimulation pulses. Based on the performance feedback from the user, the therapeutic tree (not shown) is used to guide programming of the stimulation therapy. In particular, the performance feedback directs programming through selected branches of the tree to identify a program providing desirable stimulation therapy. The term "program" generally refers to a set of stimulation parameters, such as electrode combination, electrode polarity, voltage or current amplitude, pulse width and/or pulse rate.

Stimulator 14 is implanted in patient 12 at a location minimally noticeable to the patient. For SCS, stimulator 14 may be located in the lower abdomen, lower back, or other location. Leads 16 are tunneled from stimulator 14 through tissue to reach the target tissue adjacent to spinal cord 18 for stimulation delivery. At the distal tips of leads 16 are one or more electrodes (not shown) that transfer the stimulation pulses from the lead to the tissue. The electrodes may be pad electrodes located on, for example, a paddle shaped portion of a lead 16, circular (i.e., ring) electrodes surrounding the body of leads 16, conformable electrodes, cuff electrodes, or any other type of electrodes capable of forming unipolar, bipolar or multipolar electrode configurations.

The target tissue may be any tissue affected by electrical pulses. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 perceives the interruption of pain signals as a reduction in pain and efficacious therapy. Patient 12 may perceive pain, nausea, or other discomfort resulting from the stimulation as side effects of the stimulation.

Before stimulation begins, a clinician, e.g., physician, or patient 12 may evaluate the initial condition of the patient or extent of chronic pain according to specific criteria associated with system 10. This baseline evaluation allows the clinician to compare the efficacy of the stimulation therapy and modify the therapy as needed. After system 10 is implanted in patient 12 and ready to deliver electrical stimulation therapy, the clinician programs stimulator 14 via external programmer 20. The clinician first selects an initial program that includes pre-selected stimulation parameters according to the type of stimulation needed to treat the pain of patient 12. In some embodiments, the clinician may manually select the initial stimulation parameters based upon previous experience or the baseline evaluation by patient 12.

Patient 12 may evaluate the initial stimulation parameters before further adjustments are made. In this case, the evaluation determines how the therapeutic tree is used to guide the clinician in creating a program path for chronic stimulation pain therapy. If patient 12 provides performance feedback that indicates an improvement, e.g., an improvement in efficacy, reduced or discounted as desired by the presence of side effects, which is greater than a threshold, such as 50 percent, relative to the patient's baseline condition, the clinician begins to fine tune the program path by evaluating nodes in lower levels of the therapeutic tree. If the therapy improvement is less than the threshold relative to the baseline, the clinician coarse tunes the program path by utilizing upper levels of the therapeutic tree. In other embodiments, the clinician may bypass the initial evaluation process and directly proceed to program system 10 with the therapeutic tree.

The performance feedback may be determined by a combination of elements. For example, the performance feedback may include beneficial effects, i.e., efficacy and adverse effects. Each of these effects may be weighted to indicate which effects are more important in identifying desirable therapy. In one case, adverse effects may be weighted more importantly, e.g., twice as important, as beneficial effects. In other words, adverse effects may have a greater detriment to efficacy than can be overcome with some beneficial effects. Therefore, it may be more important to minimize adverse effects than to increase beneficial effects.

The therapeutic tree is a programming mechanism that aids the clinician and patient 12 in finding effective stimulation parameters for treating the patient. The therapeutic tree includes nodes that are associated with a stimulation parameter type and a stimulation parameter type value. The nodes are arranged in different levels of the therapeutic tree. Each node is connected to one node of a higher level and at one or more nodes of a lower level. The program path begins with a first node of a first level. If the first node is selected, the program path continues to a first node of a second level. The first node of the first level may be connected to two or more nodes of the second level. Each level contains two or more nodes. Fine tuning is used to describe moving to lower levels, e.g., the second level, the third level, and so forth. The stimulation therapy is further defined as the program path increases in the number of nodes connected by the program path. A program path can only contain one node from each level of the therapeutic tree, but the program path may be reversed to create a different program path if the stimulation therapy defined by the first program path fails to effectively treat patient 12.

Each level of the therapeutic tree contains nodes that represent one stimulation parameter type. A stimulation parameter type may include electrode configuration (combination and polarity), pulse rate, pulse width, voltage amplitude, current amplitude, stimulation duration, or any other parameter that would define electrical stimulation therapy. Therefore, the multiple nodes of each level define different values for a particular stimulation parameter type value. For example, the first level may contain electrode configuration nodes, where a first node defines one electrode configuration and a second node defines a different electrode configuration. If leads 16 contain a plurality of electrodes, the first level of the therapeutic tree may contain many nodes. As described herein, the first level is named as such because it is the first level, beyond a root level defining the patient's baseline condition that the clinician would start with when creating a program path.

In some embodiments, which stimulation parameter types are placed in what levels of the therapeutic tree may be pre-configured during or shortly after manufacture of the device that utilizes or provides the tree, or configured by a field technician before system 10 is used by the clinician or patient 12. Alternatively, the clinician or patient may selectively associate parameter types at particular levels of the tree. This association of parameter types with different levels may be viewed as a prioritization of parameter types within the tree, e.g., by selecting parameter types for upper level coarse tuning. For example, the stimulation parameter types may be arranged so that higher priority adjustments occur at higher levels of the tree and lower priority adjustments occur at lower levels of the tree. In particular, the parameters may be prioritized so that parameters believed to have the largest impact on efficacy are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

In one example, the first level contains nodes specifying electrode configurations, the second level contains nodes specifying pulse rates, the third level contains nodes specifying pulse widths, and the fourth level contains nodes specifying voltage amplitudes. Hence, in this example, electrode configuration are prioritized first as having the greatest impact on efficacy, followed by pulse rate, pulse width and amplitude, all taken relative to the initial set of stimulation parameters However, more or less levels may be included in the therapeutic tree. Generally, stimulation parameter types that provide a greater change in stimulation effect are located near the first or second levels of the therapeutic tree, or higher in the tree, to provide coarse tuning. Parameter types that provide fine tuning are located at lower levels of the therapeutic tree. Stimulation parameter types not included in the therapeutic tree may be set to a default value by the factory or the clinician. In some embodiments, stimulation parameter types not included in the therapeutic tree may be added to the therapeutic tree if effective stimulation therapy is not defined by the stimulation parameter types originally included in the tree.

External programmer 20 may be a clinician programmer or a patient programmer. In some embodiments, external programmer 20 may be a computer connected to a network, where the programmer consults a network server to evaluate performance feedback and create a program path with the therapeutic tree. In the case where external programmer 20 is not connected to a network, the programmer includes the therapeutic tree in a memory such that the clinician may use the programmer to create or modify a program path at any time. If a new program path is created, the stimulation parameters, or nodes, of the new program path are transmitted to stimulator 14 to define the new stimulation therapy. External programmer 20 may retain all used programs in a memory so that the clinician can review the delivered therapies. In some embodiments, used and ineffective program paths may be removed from the therapeutic tree help guide the clinician and patient 12 to find an effective program path.

In other embodiments, a memory of stimulator 14 may store all data associated with the therapeutic tree and used program paths. External programmer 20 retrieves data from stimulator 14 to allow the clinician or patient 12 to create a program path. In this manner, all data is retained within patient 12 and multiple external programmers 24 may be used to treat the patient without storing private patient data away from the patient.

While the clinician or patient 12 may desire to manually create a program path for stimulation therapy, system 10 may provide automatic program path creation based upon the entered performance feedback. Based upon certain criteria, such as the efficacy of the current therapy, external programmer 20 may determine that the therapy is not "good enough." In some embodiments, patient 12 may indicate how much the pain has been reduced through stimulation, or how intense a side effect is, via a rating system. For example, patient 12 may enter a numerical rating on a scale of 1 to 10, with 10 indicating the pain is completely gone and 1 indicating that the pain has not been noticeably reduced. Other examples may include graphical rating systems, descriptive words selected from a list, and other methods of indicating beneficial effects, adverse effects, or other indications of stimulation performance.

In some cases, patient 12 may provide performance feedback for the stimulation therapy indirectly by providing some other type of input. For example, when stimulation is not efficacious, a patient may increase the amplitude or change other stimulation parameters in an attempt to improve the stimulation efficacy. Similarly, if a side effect is not well tolerated, a patient may decrease amplitude or change other stimulation parameters in an attempt to avoid the side effect. Stimulators or programmers according to the invention may track the frequency and type of programming changes, and use such information as performance feedback for evaluating the stimulation.

In addition, patient 12 may provide medication input to indicate the dosage and frequency of pain medication taken to reduce pain symptoms. Increased pain medication taken by patient 12 may indicate that current stimulation therapy is not effective at reducing pain symptoms. Conversely, little or no pain medication taken by patient 12 may indicate efficacious stimulation treatment.

Furthermore, sensors may be used to detect physiological parameters that can indicate if the stimulation therapy is efficacious, or if the patient is experiencing a side effect. In addition to using such information as performance feedback, stimulators or programmers may invoke tree-based programming based on therapy adjustment, medication input, or sensors signals, which may act as an indication that the stimulation therapy requires improvement. The use of a tree-based structure to improve stimulation efficacy may occur periodically, continuously, or as requested or needed throughout chronic therapy.

In cases where the therapy is rated very low, external programmer 20 may automatically move up several levels of the therapeutic tree to more quickly change the stimulation therapy. If the therapy is close to having adequate performance, external programmer 20 may only move to a different node within the same level of the tree. The therapeutic tree enables system 10 to include a feedback loop with variable instructions based upon the performance feedback, which may allow patient 12 to find the acceptable therapy in a shorter amount of time.

In some embodiments, stimulator 14 may be used in a trial mode to evaluate the efficacy of electrical stimulation. In a trial mode, finding the most effective therapy may not be necessary to prove that stimulation therapy is effective in treating patient 12. External programmer 20 may attempt to find a program path that provides a minimal amount of improvement relative to baseline conditions, e.g., a 50 percent performance feedback improvement determination, and stop modifying the therapy with the therapeutic tree. In this manner, the clinician may quickly prove reasonable therapy efficacy without the risk of further modifications to the therapy that may reduce the therapy efficacy. After the trial mode is over, external programmer 20 may resume creating new program paths in the therapeutic tree when deemed necessary from the feedback of patient 12.

Figure 2:
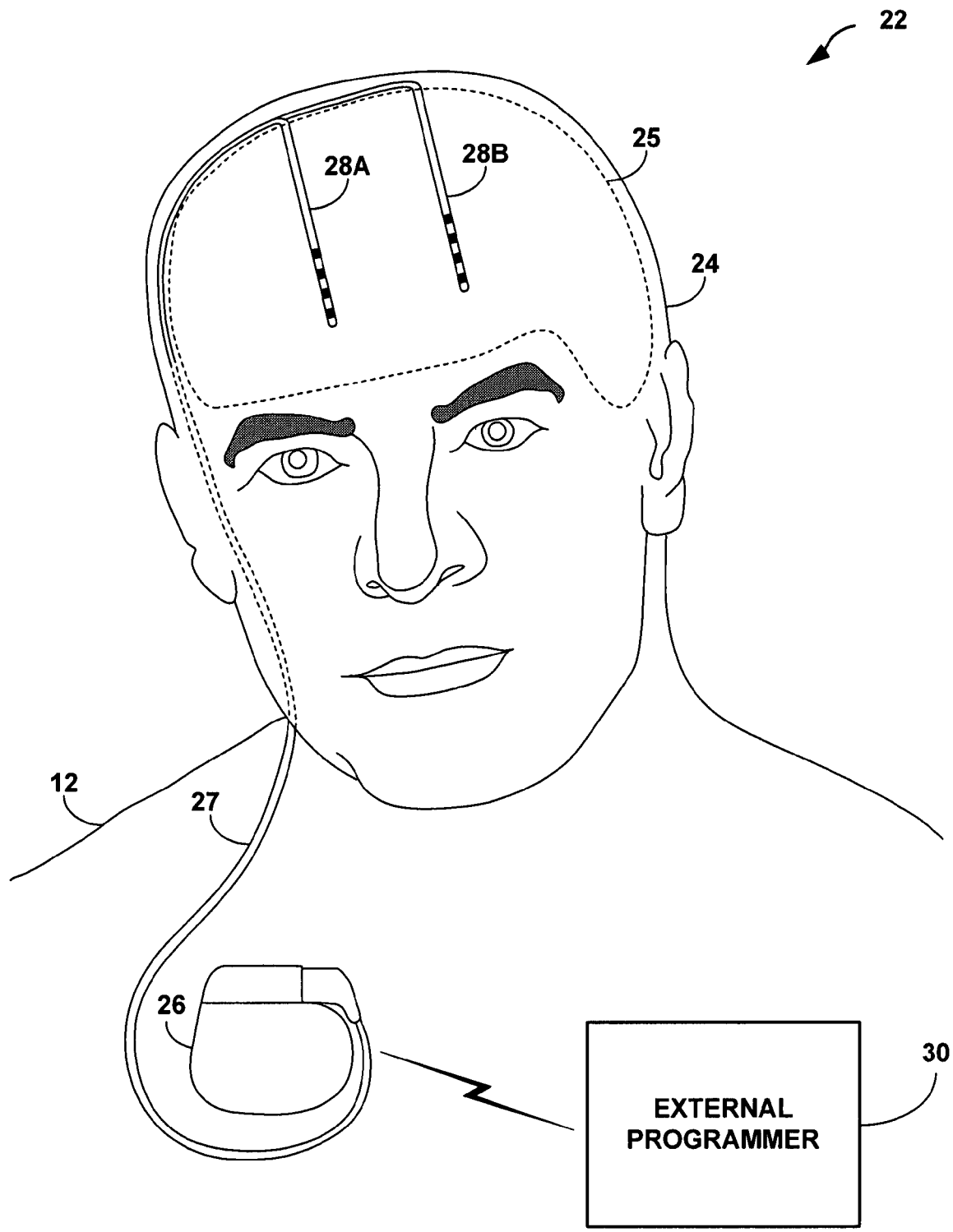
FIG. 2 is a schematic diagram illustrating an implantable deep brain stimulation system that utilizes a therapeutic tree for programming stimulation therapy.

FIG. 2 is a schematic diagram illustrating an implantable deep brain stimulation system that incorporates a therapeutic tree for programming stimulation therapy. As shown in FIG.

2, system 22 includes implantable stimulator 26 and external programmer 30 shown in conjunction with a patient 12. System 22 is similar to system 10 of FIG. 1 in using a therapeutic tree to program stimulation therapy. However, system 22 is directed to providing DBS to brain 25 of patient 12. Stimulation pulses are delivered to brain 25 in head 24 of patient 12 via one or more electrodes of leads 28A and 28B (collectively "leads 28"), where the electrode is placed adjacent to the target tissue. In the example of FIG. 2, stimulation pulses are delivered to brain 25 to reduce the symptoms of a condition, such as a movement disorder. As used herein, the term "movement disorder" refers to any disorder which may result in irregular movement, or otherwise symptomatic movement or non-movement, and includes epilepsy. Examples of movement disorders that may be treated by DBS or other stimulation therapies, and for which the stimulation may be programmed using a therapeutic tree and the techniques described herein, are tremor, Parkinson's disease, epilepsy, and spasticity.

While stimulation is shown to be delivered via two leads 28, other examples may include more or less leads. Leads 28 may have ring electrodes located at certain positions along the length of each lead. However, other examples of leads 28 may have partial ring electrodes or segmented electrodes instead of ring electrodes, such that multiple electrodes are located around the perimeter of each lead. These types of leads are referred to herein generally as having complex electrode array geometries, because their corresponding electrode combinations may be configured in three dimensions.

With reference to FIG. 2, a user, such as a clinician or patient 12, may interact with a user interface of external programmer 30 (similar to external programmer 20) to provide system 22 with performance feedback indicating the efficacy of the stimulation therapy. The performance feedback may include beneficial effects and adverse effects, which may be weighted, to determine efficacy of the therapy. Based on the performance feedback from the user, the therapeutic tree (not shown) is used to guide programming of the stimulation therapy for peripheral nerve stimulation. In particular, the performance feedback directs programming through selected branches of the tree to identify a program providing desirable therapy efficacy.

Stimulator 26 may be implanted in patient 12 at a location minimally noticeable to the patient. For DBS, stimulator 26 may be located in the upper chest, abdomen, head 24 or other locations. Lead 27 is tunneled from stimulator 26 through tissue to reach the target tissue of brain 25 for stimulation delivery. Example target tissues may include the subthalamic nucleus or substantia nigra. At the distal tip of leads 28 are one or more electrodes (not shown) that transfer the stimulation pulses from the lead to the tissue. Leads 28 and the electrodes thereon may take the form of any of the examples discussed above with reference to lead 16.

Figure 3:
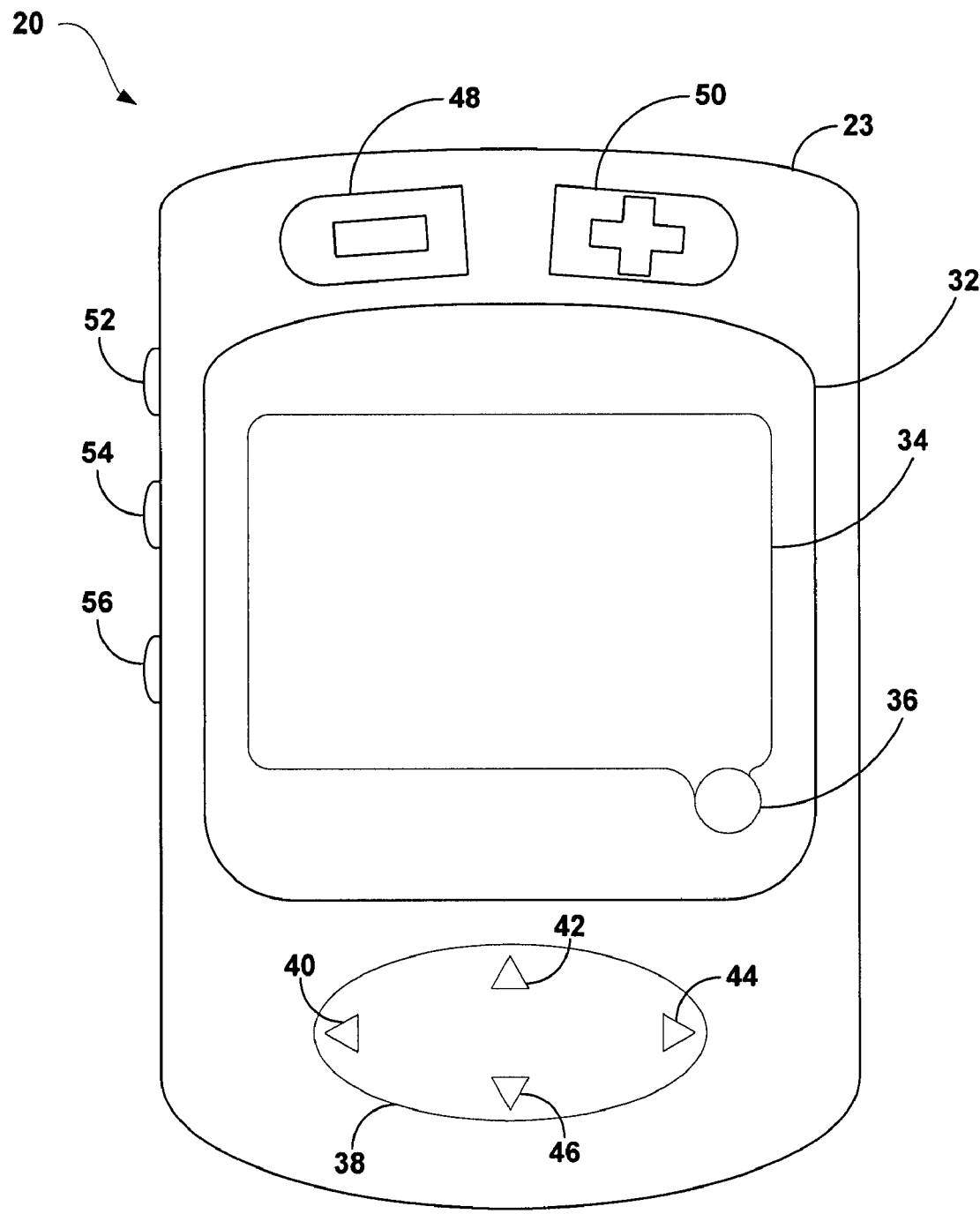
FIG. 3 is a schematic diagram illustrating an example external programmer for programming stimulation therapy.

FIG. 3 is a schematic diagram illustrating an example external programmer for programming stimulation therapy. As shown in FIG. 3, external programmer 20 provides a user interface for a user, such as patient 12, to manage and program stimulation therapy. Programmer 20 is described in FIG. 3, but programmer 30 may also be described in a similar manner. Programmer 20 is protected by housing 23 which encloses circuitry necessary for the programmer to operate. Programmer 20 also includes display 34, power button 56, increase button 50, decrease button 48, backlight 36, and select buttons 52 and 54. Cover 32 protects screen 34 from being damaged during programmer 20 use. Programmer 20 also includes control pad 38 which allows a user to navigate through items displayed on display 34 in the direction of arrows 40, 42, 44 and 46. In some embodiments, the buttons and pad may take the form of soft keys, whose functionality may change, for example, based on the current programming operation or user preference.

In the illustrated embodiment, programmer 20 is a hand held device. Programmer 20 may be a patient programmer that may accompany patient 12 at all times. In some cases, programmer 20 may be used by a clinician when patient 12 visits the clinician. In other embodiments, programmer 20 may be a clinician programmer that remains with the clinician or in the clinic, and is used by the clinician and/or patient 12 when in the patient is in the clinic.

Housing 23 may be constructed of a polymer, metal alloy, composite, or combination material suitable to protect and contain components of programmer 20. In addition, housing 23 may be partially or completely sealed such that fluids, gases, or other elements may not penetrate the housing and affect components therein. Power button 56 may turn programmer 20 on or off as desired by patient 12. Select buttons 52 and 54 may turn stimulation on and off. Backlight 36 may also control the illumination level, or backlight level, of display 34. In some embodiments, backlight 36 may be a knob that rotates clockwise and counter-clockwise to control programmer 20 operational status and display 34 illumination. Programmer 20 is prevented from turning off during telemetry with stimulator 14 or another device to prevent the loss of transmitted data or the stalling of normal operation. Alternatively, programmer 20 and stimulator 14 may include instructions which handle possible unplanned telemetry interruption, such as battery failure or inadvertent device shutdown.

Display 34 may be a liquid crystal display (LCD) or similar monochrome or color display capable of providing information, such as a user interface, to patient 12. Display 34 may provide a user interface regarding current stimulation therapy, a therapeutic tree for programming stimulation therapy, receiving feedback or medication input from patient 12, an active group of stimulation programs, and operational status of programmer 20. Control pad 38 allows patient 12 to navigate through items displayed on display 34 and/or change stimulation programs. Patient 12 may press control pad 38 on any of arrows 40, 42, 44, and 46 in order to move to another item on display 34 or move to another screen not currently shown on the display. In some embodiments, pressing the middle of control pad 38 may select any item highlighted in display 34. In other embodiments, scroll bars, a touch pad, scroll wheel, individual buttons, or a joystick may perform the complete or partial function of control pad 38.

Decrease button 48 and increase button 50 provide an input mechanism for patient 12. In general, decrease button 48 may decrease the value of a highlighted stimulation parameter every time the decrease button is pressed. In contrast, increase button 50 may increase the value of a highlighted stimulation parameter one step every time the increase button is pressed. While buttons 48 and 50 may be used to control the value of any stimulation parameter, buttons 48 and 50 may also control patient feedback input. For example, pressing increase button 50 may be efficacy input indicating that the current stimulation program is reducing pain or a movement disorder symptom. Conversely, pressing decrease button 48 may be efficacy input indicating that the current stimulation program is not reducing pain or a movement disorder symptom. In other embodiments, decrease button 48 and increase button 50 may only decrease and increase stimulation parameters while control pad 38 is used to receive performance feedback from patient 12 or a clinician.

Select buttons 42 and 44 may be configured to perform operational functions related to stimulation therapy or the use of programmer 20. For example, buttons 42 and 44 may control the volume of audible sounds produced by programmer 20, wherein button 42 increases the volume and button 44 decreases the volume. Button 46 may be pressed to enter an operational menu that allows patient 12 to configure the user interface of programmer 20 to the desires of patient 12. For example, patient 12 may be able to select a language, backlight delay time, display 24 brightness and contrast, or other similar options. In alternative embodiments, buttons 38 and 40 may control all operational and selection functions, such as those related to audio volume or stimulation therapy.

Programmer 20 may take other shapes or sizes not described herein. For example, programmer 20 may take the form of a clam-shell shape, similar to cellular phone designs. When programmer 20 is closed, some or all elements of the user interface may be protected within the programmer. When programmer 20 is opened, one side of the programmer may contain a display while the other side may contain input mechanisms. In any shape, programmer 20 may be capable of performing the requirements described herein. Alternative embodiments of programmer 20 may include other input mechanisms such as a keypad, microphone, camera lens, or any other input media that allows the user to interact with the user interface provided by programmer 20.

In alternative embodiments, the buttons of programmer 20 may perform different functions than the functions provided in FIG. 3 as an example. In addition, other embodiments of programmer 20 may include different button layouts or number of buttons. For example, programmer 20 may even include a single touch screen that incorporates all user interface functionality.

Figure 4:
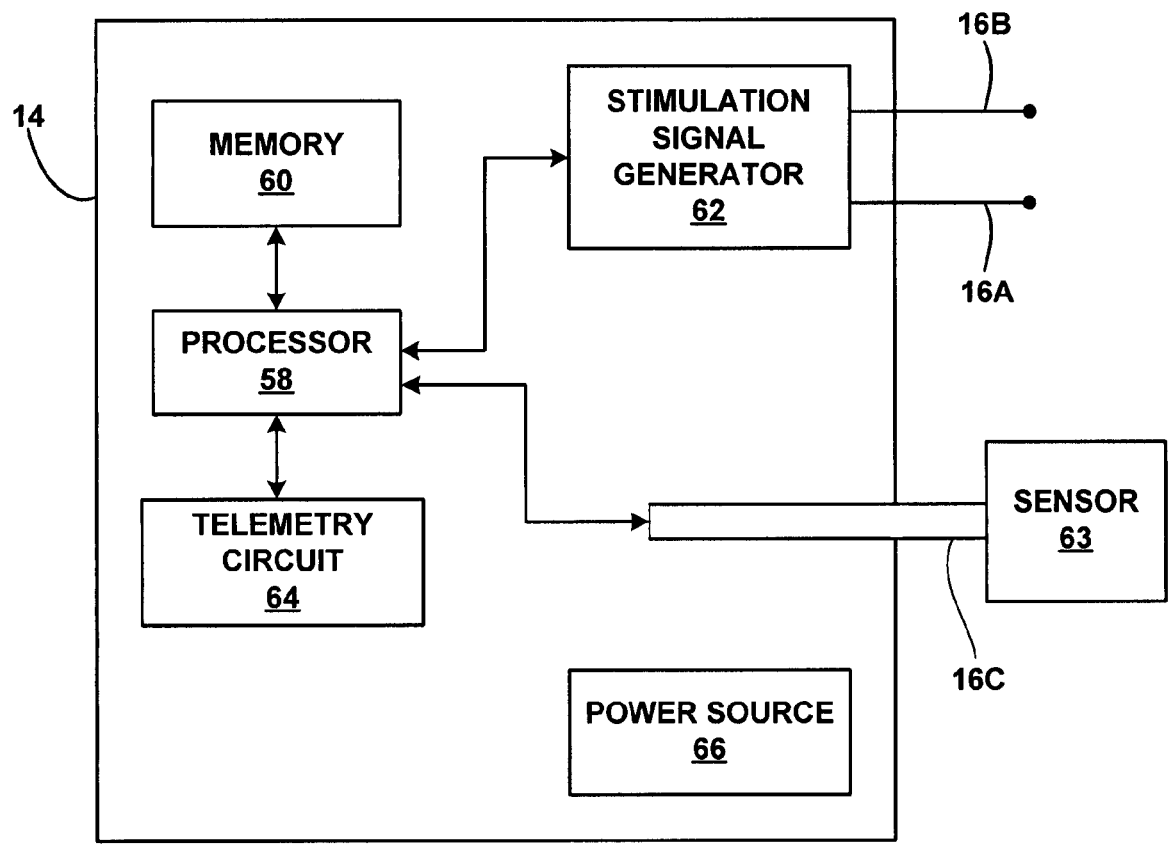
FIG. 4 is a functional block diagram illustrating various components of an implantable stimulator that communicates wirelessly with an external programmer.

FIG. 4 is a functional block diagram illustrating various components of implantable stimulator 14, which may communicate wirelessly with an external programmer. Stimulator 14 may be substantially similar to stimulator 26 of FIG. 2. In the example of FIG. 4, stimulator 14 includes a processor 58, memory 60, stimulation signal generator 62, sensor 63, telemetry circuit 64, sensor 63, and power source 66. Memory 60 may store instructions for execution by processor 58, stimulation therapy data, performance feedback, and any other information regarding therapy or patient 12. Therapy information may be recorded for long-term storage and retrieval by a user, and adjustment of the program path of the therapeutic tree. Memory 60 may include separate memories for storing instructions, the therapeutic tree, program path, and program histories.

Processor 58 controls stimulation signal generator 62 to deliver electrical stimulation therapy via one or more leads 16. An exemplary range of neurostimulation stimulation parameters likely to be effective in treating chronic pain, e.g., when applied to spinal cord 18, are listed below. While stimulation pulses are described, stimulation signals may be of any forms such as sine waves or the like.

1. Frequency: between approximately 0.5 Hz and 2000 Hz, more preferably between approximately 30 Hz and 250 Hz, and still more preferably between approximately 60 Hz and 150 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage is delivered.

3. Pulse Width: between about 10 microseconds and 5000 microseconds, more preferably between approximately 100 microseconds and 1000 microseconds, and still more preferably between approximately 180 microseconds and 450 microseconds.

In some embodiments, processor 58 modifies the current program path or stimulation parameters stored in memory 60 based on traversal of the therapeutic tree and performance feedback using the techniques described herein. In some embodiments, another device, such as programmer 20, 30, modifies the current program path or stimulation parameters stored in memory 60 based on traversal of the therapeutic tree and performance feedback. In such embodiments, processor 58 may receive modification of the stimulation parameters from the other device via telemetry circuit 64, and store the modified stimulation parameters in memory 60.

In either case, processor 58 controls stimulation signal generator 62 to provide electrical stimulation according to the stimulation parameters stored in memory 60, which may be determined based on the current program path of the therapeutic tree. Processor 58 may determine that a new program path should be created, among other reasons, based on information regarding the operation of electrodes and the leads 16. If one or more electrodes becomes damaged or inoperable, processor 58 may eliminate a particular node from the therapeutic tree, or indicate to another device via telemetry circuit 64 that a particular node should be removed from the tree. If the damaged electrode is used by the current program, processor 58 or another device may select an electrode configuration or combination node nearest the current program path of the therapeutic tree, or stop stimulation until a new program path is determined with efficacy feedback from patient 12, the clinician, or a sensor.

Processor 58 may include a microprocessor, a controller, a digital signal processor (DSP), an application specific integrated circuit (ASIC), a field-programmable gate array (FPGA), discrete logic circuitry, or the like. Memory 60 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 60 stores program instructions that, when executed by processor 58, cause stimulator 14 and processor 58 to perform the functions attributed to them herein.

In some embodiments, the therapeutic tree may be traversed based on subjective performance feedback received from a patient or clinician that may include beneficial effects and adverse effects from therapy. Processor 58 may additionally or alternatively receive measurements or signals from sensor 63 that are indicative of one or more physiological parameters of patient 12. Such physiological parameter measurements or signals may be used by processor 58 or other devices, such as a programmer 20, 30, as objective performance feedback for traversal of the therapeutic tree. Sensor 63 may be used for objective measurements of beneficial effects and/or adverse effects.

Sensor 63 generates a signal as a function of one or more physiological parameters of a patient 12. Stimulator 14 may include circuitry (not shown) that conditions the signals generated by sensors 63 such that they may be analyzed by processor 58. For example, stimulator 14 may include one or more analog to digital converters to convert analog signals generated by sensor 63 into digital signals usable by processor 58, as well as suitable filter and amplifier circuitry. Although shown as including one sensor 63, system 10 may include any number of sensors.

Further, as illustrated in FIG. 4, sensor 63 may be included as part of stimulator 14, or coupled to the stimulator via lead 16C, which may or may not include electrodes for delivering stimulation. In some embodiments, a sensor 63 located outside of stimulator 14 may be in wireless communication with processor 58. Wireless communication between sensor 63 and stimulator 14 may, as examples, include radio frequency (RF) communication or communication via electrical signals conducted through the tissue and/or fluid of a patient 12.

A variety of physiological parameters of patient 12 may vary based upon the symptoms experienced by the patient, e.g., pain or disordered movement, and thus based upon the efficacy of the stimulation delivered by stimulator 14. Accordingly, signals generated by one or more sensors 63 may reflect the efficacy of stimulation. One or more components of a system 10, 22 according to the invention may monitor signals generated by sensors 63 as performance feedback for the purpose of traversing a therapeutic tree to identify stimulation parameters according to the techniques described herein.

Example physiological parameters of patient 12 that may be monitored by a stimulator 14 via one or more sensors 63 include activity, posture, motion heart rate, electrocardiogram (ECG) morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids, brain electrical activity, and eye motion. In some embodiments, speech may be monitored. Further, in some external medical device embodiments of the invention, galvanic skin response may additionally or alternatively be monitored. Sensor 63 may be of any type known in the art capable of generating a signal as a function of one or more of these parameters.

The activity level of patient 12 may vary based on the severity of symptoms experienced by the patient. A patient in pain or experiencing substantial movement disorder symptoms may avoid activity and, conversely, as symptoms are alleviated may engage in greater activity. Accordingly, the activity level of patient 12 may indicate the efficacy of stimulation, and may be used as performance feedback for traversal of a therapeutic tree according to the techniques described herein.

Stimulator 14 may include one or more sensors 63 that generate a signal as a function of patient activity. For example, sensors 63 may include one or more accelerometers, gyros, mercury switches, or bonded piezoelectric crystals that generates a signal as a function of patient activity, e.g., body motion, footfalls or other impact events, and the like. Additionally or alternatively, sensors 63 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to stimulator 14 wirelessly or by leads 16 or, if stimulator 14 is implanted in these locations, integrated with a housing of stimulator 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to stimulator 14 wirelessly or via leads 16, or piezoelectric crystals may be bonded to the can of stimulator 14 when the stimulator is implanted in these areas, e.g., in the back, chest, buttocks or abdomen of a patient 12. Processor 58 may also detect spasmodic or pain related muscle activation, tremor, or other disordered movements via the signals generated by such sensors.

In some embodiments, the activity level of a patient may be determined by monitoring another physiological parameter that varies as a function of patient activity. For example, sensor 63 may include electrodes located on leads or integrated as part of the housing of stimulator 14 that generate an electrogram signal as a function of electrical activity of the heart of a patient 12, and processor 58 may monitor the heart rate of the patient 12 based on the electrogram signal. In other embodiments, a sensor 63 may include an acoustic sensor within stimulator 14, a pressure or flow sensor within the bloodstream or cerebrospinal fluid of a patient 12, or a temperature sensor located within the bloodstream of the patient 12. The signals generated by such sensors may vary as a function of contraction of the heart of a patient 12, and can be used by processor 58 to monitor the heart rate of the patient 12.

In some embodiments, processor 58 may detect, and measure values for one or more ECG morphological features within an electrogram generated by electrodes as described above. ECG morphological features may vary based on patient activity. For example, the amplitude of the ST segment of the ECG may increase as patient activity increases. Further, the amplitude of a QRS complex or T-wave may increase, and the widths of the QRS complex and T-wave may decrease as patient activity increases.

Additionally, the respiration rate and volume of patient 12 increase with increasing activity by the patient. In some embodiments, sensor 63 may include an electrode pair, including one electrode integrated with the housing of stimulator 14 and one of the electrodes of leads 16 that generate a signal as a function of the thoracic impedance of a patient 12, which varies as a function of respiration by the patient 12. In other embodiments, sensor 63 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate or volume.

Sensor 63 may include any of a variety of known temperature sensors to generate a signal as a function of a core or subcutaneous temperature of a patient 12, which varies based on patient activity. Such electrodes and temperature sensors may be incorporated within the housing of stimulator 14, or coupled to the stimulator wirelessly or via leads. Sensor 63 may also include a pressure sensor within, or in contact with, a blood vessel. The pressure sensor may generate a signal as a function of the a blood pressure of a patient 12, which varies based on patient activity, and may, for example, comprise a Chronicle Hemodynamic Monitor™ commercially available from Medtronic, Inc. of Minneapolis, Minn.

Sensor 63 may also include optical pulse oximetry sensors or Clark dissolved oxygen sensors located within, as part of a housing of, or outside of stimulator 14, which generates signals as a function of blood oxygen saturation and blood oxygen partial pressure respectively. In some embodiments, a system 10 may include a catheter with a distal portion located within the cerebrospinal fluid of a patient 12, and the distal end may include a Clark dissolved oxygen sensor to generate a signal as a function of the partial pressure of oxygen within the CSF. Blood oxygen saturation, and blood or CSF oxygen partial pressure, varies based on patient activity.

In some embodiments, sensor 63 may include one or more intraluminal, extraluminal, or external flow sensors positioned to generate a signal as a function of arterial blood flow, which varies based on patient activity level. A flow sensor may be, for example, an electromagnetic, thermal convection, ultrasonic-Doppler, or laser-Doppler flow sensor. Further, in some external medical device embodiments of the invention, sensor 63 may include one or more electrodes positioned on the skin of a patient 12 to generate a signal as a function of galvanic skin response, which reflects patient activity level.

When a patient is in pain, the patient may avoid particular postures, or transition between postures as a result of activity less frequently. Accordingly, posture and frequency of posture transitions of patient 12 may reflect the efficacy of stimulation therapy delivered by stimulator 14 to treat pain, and may be used as performance feedback for traversal of a therapeutic tree according to the techniques described herein.

In some embodiments, sensor 63 may include a plurality of accelerometers, gyros, or magnetometers oriented orthogonally that generate signals which indicate the posture of a patient 12. In addition to being oriented orthogonally with respect to each other, sensor 63 is used to detect the posture of a patient 12 may be generally aligned with an axis of the body of the patient 12. In exemplary embodiments, stimulator 14 includes three orthogonally oriented posture sensors 63.

When sensor 63 include accelerometers, for example, that are aligned in this manner, processor 58 may monitor the magnitude and polarity of DC components of the signals generated by the accelerometers to determine the orientation of a patient 12 relative to the Earth's gravity, e.g., the posture of the patient 12. In particular, the processor 58 may compare the DC components of the signals to respective threshold values stored in memory 60 to determine whether a patient 12 is or is not recumbent. Further information regarding use of orthogonally aligned accelerometers to determine patient posture may be found in a commonly assigned U.S. Pat. No. 5,593,431, which issued to Todd J. Sheldon. Another sensor 63 that may generate a signal that indicates the posture of a patient 12 include electrodes that generate an electromyogram (EMG) signal, or bonded piezoelectric crystals that generate a signal as a function of contraction of muscles. Such sensor 63 may be implanted in the legs, buttocks, abdomen, or back of a patient 12, as described above. The signals generated by such sensors when implanted in these locations may vary based on the posture of a patient 12, e.g., may vary based on whether the patient is standing, sitting, or lying down.

Further, the posture of a patient 12 may affect the thoracic impedance of the patient. Consequently, sensor 63 may include an electrode pair, including one electrode integrated with the housing of an stimulator 14 and one of electrodes on leads 16, that generates a signal as a function of the thoracic impedance of the patient 12, and processor 58 may detect the posture or posture changes of the patient 12 based on the signal. The electrodes of the pair may be located on opposite sides of the patient's thorax. For example, the electrode pair may include one of the electrodes located proximate to the spine of a patient for delivery of SCS therapy, and stimulator 14 with an electrode integrated in its housing may be implanted in the abdomen of a patient 12.

Additionally, changes of the posture of a patient 12 may cause pressure changes with the CSF of the patient. Consequently, sensor 63 may include pressure sensors coupled to one or more intrathecal or intracerebroventricular catheters, or pressure sensors coupled to stimulator 14 wirelessly or via any of leads 16. CSF pressure changes associated with posture changes may be particularly evident within the brain of the patient, e.g., may be particularly apparent in an intracranial pressure (ICP) waveform.

In addition to activity level and posture, the quality of sleep experienced by patient 12 may reflect the performance of stimulation parameters. More particularly, symptoms such as pain and disordered movement negatively affect the quality of sleep experienced by patient 12. In some embodiments, to monitor sleep quality as performance feedback, processor 58 may identify when a patient 12 is attempting to sleep and/or asleep. For example, processor 58 may identify the time that patient begins attempting to fall asleep based on an indication received from a patient 12, e.g., via programmer 20, 30 and a telemetry circuit 64. In other embodiments, processor 58 identifies the time that a patient 12 begins attempting to fall asleep, falls asleep and/or wakes up based on the activity level, posture, or other physiological parameters of the patient 12.

In order to determine when patient 12 is attempting to sleep and asleep, processor 58 may identify a time when the activity level of a patient 12 falls below a threshold activity level value stored in memory 60, and may determine whether the activity level remains substantially below the threshold activity level value for a threshold amount of time stored in memory 60. In other words, a patient 12 remaining inactive for a sufficient period of time may indicate that patient 12 is attempting to fall asleep. If processor 58 determines that the threshold amount of time is exceeded, processor 58 may identify the time at which the activity level fell below the threshold activity level value as the time that a patient 12 began attempting to fall asleep. Furthermore, processor 58 may determine when patient 12 awakes based on the activity level exceeding a threshold level, or exceeding the threshold level for a threshold period of time. Such thresholds may be stored in memory 60.

In some embodiments, processor 58 determines whether a patient 12 is attempting to fall asleep, asleep, or awake based on whether the patient 12 is or is not recumbent, e.g., lying down, using posture sensors 63 as described above. In some embodiments, processor 58 considers both the posture and the activity level of patient 12 when determining whether a patient 12 is attempting to fall asleep or is asleep. For example, processor 58 may determine whether a patient 12 is attempting to fall asleep based on a sufficiently long period of sub-threshold activity, as described above, and may identify the time that patient began attempting to fall asleep as the time when a patient 12 became recumbent. Any of a variety of combinations or variations of these techniques may be used to determine when a patient 12 is attempting to fall asleep, and a specific one or more techniques may be selected based on the sleeping and activity habits of a particular patient.

In other embodiments, processor 58 determines when a patient 12 is attempting to fall asleep based on the level of melatonin in a bodily fluid. In such embodiments, sensor 63 may take the form of a chemical sensor that is sensitive to the level of melatonin or a metabolite of melatonin in the bodily fluid, and estimate the time that a patient 12 will attempt to fall asleep based on the detection. For example, processor 58 may compare the melatonin level or rate of change in the melatonin level to a threshold level stored in memory 60, and identify the time that threshold value is exceeded. Processor 58 may identify the time that a patient 12 is attempting to fall asleep as the time that the threshold is exceeded, or some amount of time after the threshold is exceeded.

Processor 58 may also determine when a patient 12 is asleep based on other physiological parameters sensed by one or more sensors 63. Detected values of physiological parameters of a patient 12, such as heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when a patient 12 falls asleep or awakes. Some of these physiological parameters may be at low values when a patient 12 is asleep. Further, the variability of at least some of these parameters, such as heart rate and respiration rate, may be at a low value when the patient is asleep.

Consequently, in order to detect when a patient 12 falls asleep and wakes up, processor 58 may monitor one or more of these physiological parameters, or the variability of these physiological parameters, and detect the discernable changes in their values associated with a transition between a sleeping state and an awake state. In some embodiments, processor 58 may determine a mean or median value for a parameter based on values of a signal over time, and determine whether a patient 12 is asleep or awake based on the mean or median value. Processor 58 may compare one or more parameter or parameter variability values to thresholds stored in memory 60 to detect when a patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 58 to determine whether a patient 12 is asleep may include a time component. For example, a threshold may require that a physiological parameter be above or below a threshold value for a period of time before processor 58 determines that patient is awake or asleep.

Additionally, in some embodiments, sensor 63 may include one or more electrodes positioned within or proximate to the brain of patient, which detect electrical activity of the brain. For example, in embodiments in which stimulator 14 delivers stimulation to the brain, processor 58 may be coupled to electrodes implanted on or within the brain via leads 16. Processor 58 may determine whether patient is asleep or awake based on the electrical activity of the brain of patient 12, e.g., an electroencephalogram (EEG) of patient 12, detected by such sensors 63. Furthermore, processor 58 may determine within which sleep state, e.g., S1-S4 or rapid eye movement (REM), patient 12 is based on the EEG or any one or more of the other physiological parameters discussed above.

Processor 58, or another device in systems 10, 22, may determine values for any of a variety of metrics indicative of sleep quality based on identification of when patient 12 is attempting to sleep, asleep, within particular sleep states, or awake. Such sleep quality metrics may be used by processor 58 or another device as performance feedback for traversal of a therapeutic tree and identification of stimulation parameter values. As examples, processor 58 may determine the amount or percentage of time asleep or in particular sleep states, the length or frequency of arousals or other disturbances during sleep, the length of time attempting to sleep prior to falling asleep (sleep latency), or the percentage of time asleep when attempting to sleep (sleep efficiency). Sensor 63 may be any of the sensors, and processor 58 may monitor any of physiological parameters and determine any of the sleep quality metrics described in commonly-assigned and co-pending application Ser. No. 11/691,376, by Miesel et al., entitled "COLLECTING SLEEP QUALITY INFORMATION VIA A MEDICAL DEVICE," filed Mar. 26, 2007, the entire content of which is incorporated herein by reference.

Processor 58, or another device in systems 10, 22, may determine values for any of a variety of metrics indicative of activity level, posture, or posture transitions based on the physiological parameters and sensor 63 signals discussed above. Such activity and posture metrics may be used by processor 58 or another device as performance feedback for traversal of a therapeutic tree and identification of stimulation parameter values. Sensor 63 may be any of the sensors, and processor 58 may monitor any of physiological parameters and determine any of the posture and activity metrics described in commonly-assigned and co-pending application Ser. No. 11/691,411, by Miesel et al., entitled "COLLECTING ACTIVITY INFORMATION TO EVALUATE THERAPY;" and commonly-assigned and co-pending application Ser. No. 11/691,391, by Miesel et al., entitled "COLLECTING POSTURE INFORMATION TO EVALUATE THERAPY." Both of these applications were filed on Mar. 26, 2007, and their entire content is incorporated herein by reference.

As discussed above, performance feedback for pain, movement disorders, or other disorders may be received via sensors 63. For movement disorders, performance feedback may include efficacy feedback regarding the extent of disordered movement. The extent of disordered movement may be evaluated based on signals from a variety of the sensors 63 discussed above, including accelerometers, piezoelectric elements, and EMG electrodes, which may be located at any of a variety of locations in the body of a patient, including the trunk, head or limbs. Such sensors may detect, as examples, tremor or gait irregularity. Furthermore, the extent of symptoms of movement disorders or other neurological disorders may be detected based on neurological activity via a sensor 63 that takes the form of EEG electrodes. In some cases, particular patterns or other indicators in the EEG may be used to detect, for example, seizure or tremor.

Furthermore, in addition to efficacy or positive effect performance feedback, such sensors 64 may be used as adverse effect feedback in some embodiments. For example, irregular gait or other movement, or general lack of activity, may be or indicate an adverse effect of stimulation therapy, whether for pain, movement disorders, DBS, or some other therapy. Other adverse effects that may be detected via sensors 63 include speech difficulty, which may be detected via a microphone, as an example. As examples, frequency, patterns, clarity or the like, may be compared In some examples, processor 58 may be able to manage the power consumption of stimulation therapy using a therapeutic tree. Each node in the therapeutic tree may be weighted according to power usage values, which is a system performance value, for the particular parameter of the node. Alternatively, a second therapeutic tree may be used after identifying a program path in the first therapeutic tree in order to optimize the power consumption of the stimulation therapy. In either case, the therapeutic tree may be used to weight and organize power usage values to minimize the consumption of power during therapy. For example, once an electrode configuration is selected, the levels of the therapeutic tree may continue from pulse rate, to pulse width, to amplitude.

Wireless telemetry in stimulator 14 with external programmer 20 or another device may be accomplished by RF communication or proximal inductive interaction of stimulator 14 with external programmer 20. Accordingly, telemetry circuit 64 may send information to external programmer 20 on a continuous basis, at periodic intervals, or upon request from the implantable stimulator or programmer. Wireless telemetry may be accomplished by RF communication or proximal inductive interaction of stimulator 14 with external programmer 20.

Power source 66 delivers operating power to the components of stimulator 14. Power source 66 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional batteries may be used for a limited period of time. As a further alternative, an external inductive power supply could transcutaneously power stimulator 14 whenever measurements are needed or desired.

Figure 5:
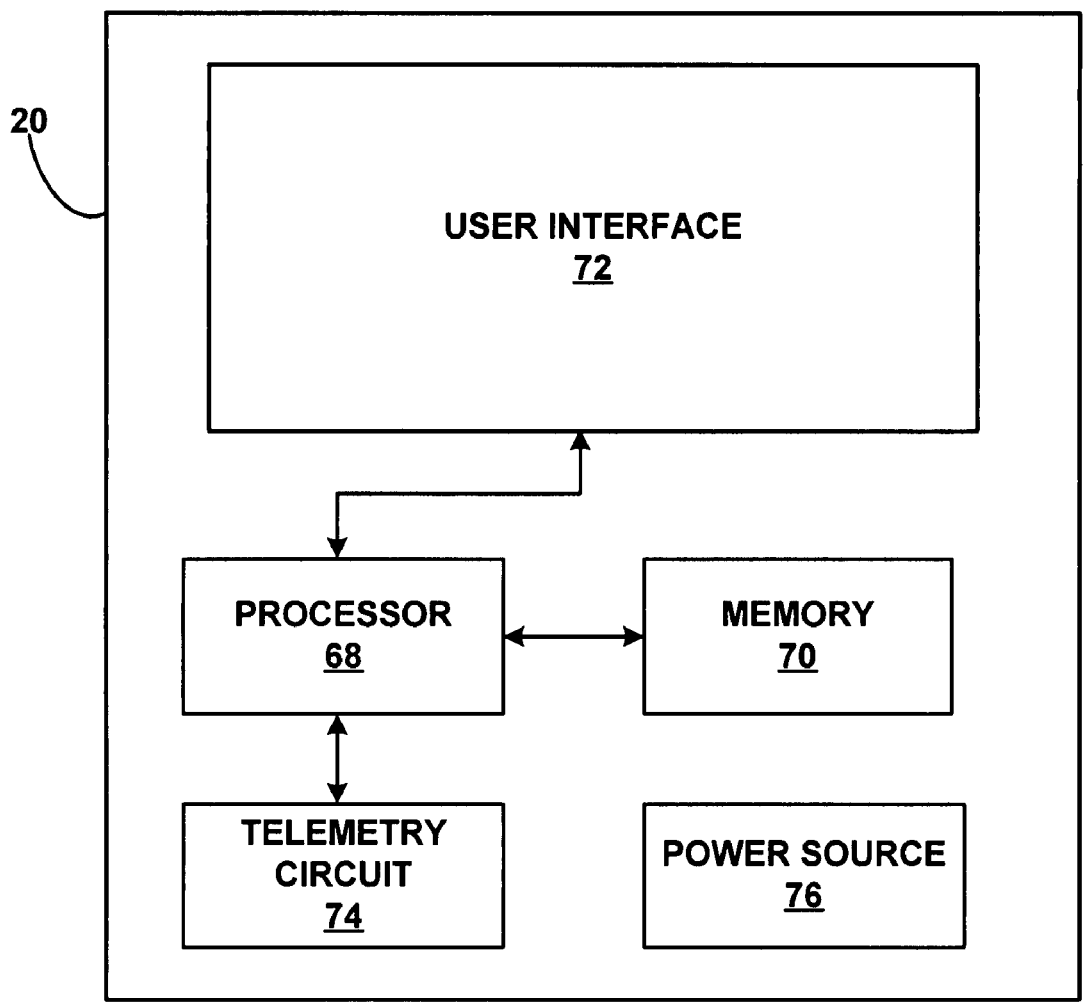
FIG. 5 is a functional block diagram illustrating various components of an external programmer that communicates wirelessly with the implantable stimulator.

FIG. 5 is a functional block diagram illustrating various components of an external programmer that communicates wirelessly with the implantable stimulator. As shown in FIG. 5, external programmer 20 includes processor 68, memory 70, telemetry circuit 74, user interface 72, and power source 76. The clinician or patient 12 interacts with user interface 72 in order to manually change the program path, adjust voltage or current amplitude, change weighting (i.e., prioritization or level) of stimulation parameter types within the therapeutic tree, provide efficacy feedback, or view stimulation data.

User interface may include a screen and one or more input buttons that allow external programmer 20 to receive input from a user. The screen may be a liquid crystal display (LCD), dot matrix display, or touch screen. The input buttons may include a touch pad, increase and decrease buttons, emergency shut off button, and other buttons needed to control the stimulation therapy, as described above with regard to FIG. 3. The clinician and patient 12 may provide therapy performance feedback information, such as pain levels or medication taken, so that the therapeutic tree may be used to create an effective program path for the patient.

Processor 68 controls user interface 72, retrieves data from memory 70 and stores data within the memory. Processor 68 also controls the transmission of data through telemetry circuit 74 to stimulator 14. Memory 70 includes operation instructions for processor 68 and, in some embodiments, data related to the structure of the therapeutic tree and currently chosen program path. Memory 70 may also include a history of all tested or used program paths and performance feedback input. Memory 70 may be a computer-readable medium comprising program instructions that cause processor 68 and programmer 20 to provide any of the functionality ascribed to them, and perform any of the methods described herein.

Telemetry circuit 74 allows the transfer of data to and from stimulator 14. Telemetry circuit 74 may communicate automatically with stimulator 14 at a scheduled time or when the telemetry circuit detects the proximity of the stimulator. Alternatively, telemetry circuit 74 may communicate with stimulator 14 when signaled by a user through user interface 72. Power source 76 may be a rechargeable battery, such as a lithium ion or nickel metal hydride battery. Other rechargeable or conventional batteries may also be used. In some cases, external programmer 20 may be used when coupled to an alternating current outlet.

In some embodiments, processor 68 may traverse a therapeutic tree based on performance feedback to identify stimulation parameters according to any of the techniques described herein. In some embodiments, performance feedback may take the form of patient or clinician feedback received via user interface 72. Additionally or alternatively, performance feedback may take the form of signals from one or more sensors 63, or information derived therefrom.

In some embodiments, processor 68 may receive such signals or information from stimulator 14. In other embodiments, processor 68 may receive the signals directly from sensors 63. For example, sensors 63 may be included within, or wired or wirelessly coupled to a programmer 20, 30.

Figure 6:
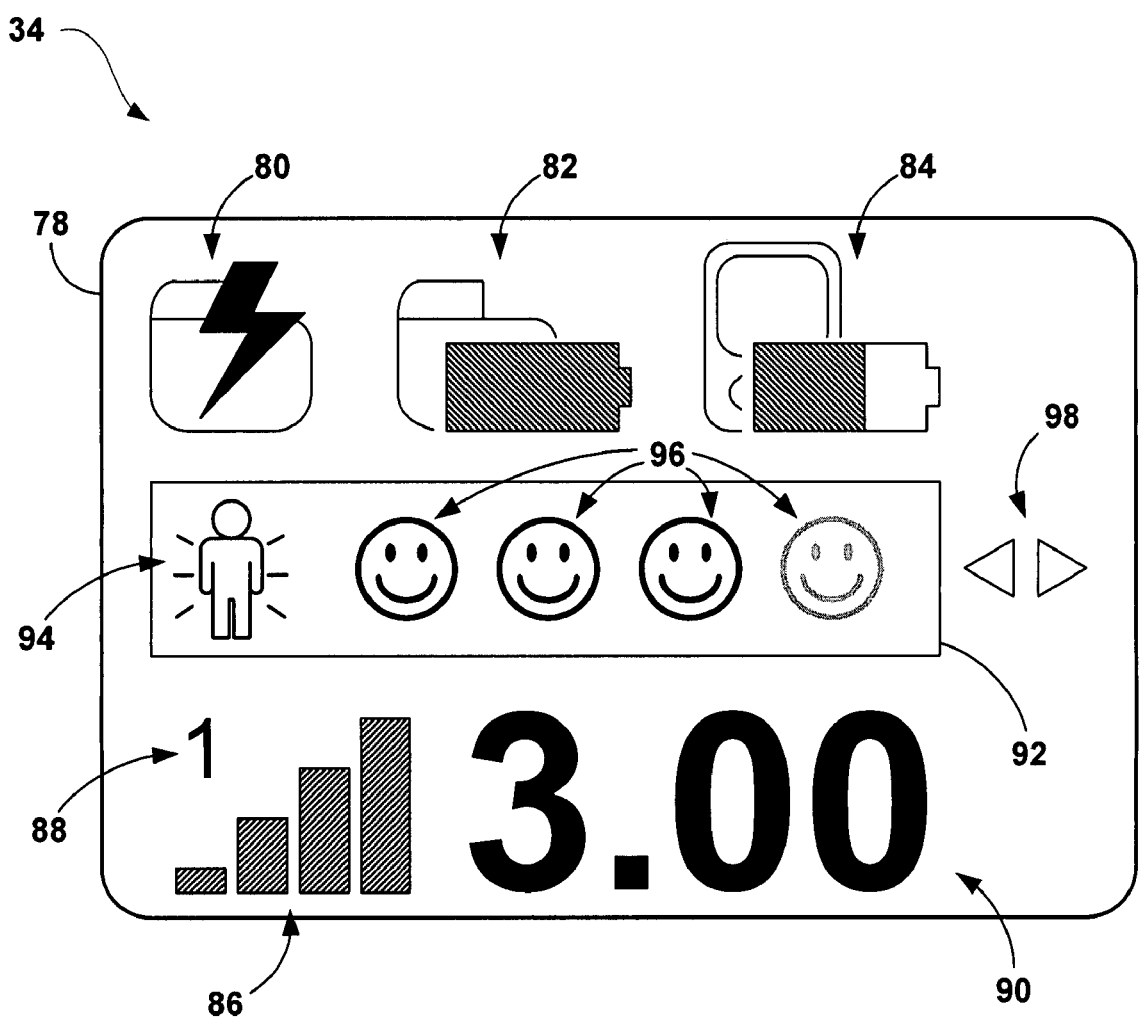
FIG. 6 is an example user interface for receiving performance feedback as patient input.

FIG. 6 is an example user interface for receiving patient or clinician input indicating therapy performance feedback as perceived by the patient. In the example of FIG. 6, display 34 of programmer 20 provides user interface 78 to the user, such as patient 12. User interface 78 includes program number 88, parameter icon 86, information box 92, voltage amplitude 90, navigation arrows 98, stimulation icon 80, battery icon 82, and programmer battery 84. User interface 78 provides information to patient 12 regarding stimulation status and feedback input from the patient. More or less information may be provided to patient 12, as desired by the clinician or patient.

Program number 88 and parameter icon 86 indicate the stimulation program currently used to provide stimulation therapy. In the example of FIG. 6, the program may be defined by the program path of a therapeutic tree. The therapeutic tree may also be used to change stimulation parameters of an existing program or create a new program from an existing program. Multiple programs may be created with the therapeutic tree and stored within programmer 20 and/or stimulator 14. In this manner, patient 12 may select from multiple stimulation programs for certain times of days, postures, activities, or other circumstances where a variation in stimulation may provide improved therapy.

Information box 92 contains information regarding the current stimulation program or programming effort. In the example of FIG. 6, information box 92 displays an indication of beneficial effects from patient 12. Effect icon 94 indicates to the user that information box 92 is showing efficacy input that patient 12 has provided regarding the current stimulation therapy. Specifically, the efficacy input is shows as beneficial effects. Smile icons 96 indicate that the current stimulation therapy provides some beneficial effects in treating patient 12. As shown, three smile icons 96 indicates that patient 12 perceives little remaining symptoms during the therapy. The fourth smile icon 96 is grayed out because patient 12 has only indicated that the therapy is effective at eliminating most of the patient's symptoms. Fewer smile icons 96 may indicate that therapy is reducing symptoms but that some symptoms remain, while all four smile icons 96 indicates that the patient 12 cannot perceive any remaining symptoms. The number of smile icons 96 selected by patient 12 may indicate a percent efficacy of the therapy for beneficial effects. For example, two smile icons 96 may indicate that the therapy is 50 percent effective. Generally, patient 12 or the clinician may continue creating new programs with the therapeutic tree until the program provides at least 50 percent efficacy, approximately equal to two smile icons 96. Patient 12 may indicate one smile face 96 for every press of increase button 50 of programmer 20, for example. Conversely, user interface 78 may be used to receive input regarding adverse effects from stimulation therapy. The user may navigate to an additional screen that prompts the user to provide simple feedback indicating adverse effects. Frown icons may be shown to indicate that the therapy is creating some adverse effects. Further, multiple frown icons may indicate that stimulation therapy is increasing adverse effects, such as pain, further unwanted movements, speech problems, loss of sight, or other unwanted effects due to the therapy. In this case, programmer 20 may move within the therapeutic tree to attempt to find more efficacious stimulation parameters for treating the patient to minimize the adverse effects. Further, programmer 20 may weight beneficial effects and adverse effects in order to optimize the feedback for efficacious therapy. In alternative examples, information box 92 may include numbers, letters, text, symbols, or any other indicator for the efficacy input provided by patient 12 or the clinician.

Voltage amplitude 90 displays the current voltage amplitude of the selected program 1 as shown by program number 88. Currently, the voltage amplitude is shown to be at 3.00 volts. If the voltage amplitude was at a maximum or minimum limit, a limit icon (not shown) may be displayed. In other embodiments, voltage amplitude 108 may display more or less decimal places to show amplitude precision as necessary for the stimulation therapy. Further, voltage amplitude 108 may be shown with graphs or text instead of numerals. In alternative embodiments where current amplitude, pulse rate, or pulse width may be adjusted, those parameter values may be displayed in place of voltage amplitude 108. In addition, patient 12 may make selections via user interface 78 to show the value of a desired one of a plurality of parameters and adjust it.

Stimulation icon 80 indicates the current status of stimulation therapy. Currently, the bolt is shown to indicate that stimulation is being delivered to patient 12 according to the active program group, i.e., program 1. In the case that stimulation is not being delivered, the bolt in icon 80 may not be shown. Stimulator battery 82 indicates the status of the battery in stimulator 14, which currently indicates that the battery is fully charged, or has a full charge in the case that the battery is not rechargeable. In other embodiments of stimulator battery 82, a percentage of battery life or battery life time remaining may be shown. Similar to stimulator battery 82, programmer battery 84 indicates the status of the battery in programmer 20. Currently, programmer battery 116 displays that the programmer battery has approximately two-thirds charge remaining. In alternative embodiments, other status indications may be used to show a percentage or time remaining of the programmer battery.

Arrows 98 provide a method for patient 12 to navigate to another screen or user interface of display 34. Patient 12 may highlight arrows 98, e.g., with a stylus or a button, and select it to move to another screen. In a similar manner, patient 12 may highlight other icons or areas of user interface 78 to make modifications to the associated aspects of the stimulation therapy. The components of user interface 78 are provided as an exemplary screen for a single program, while other layouts or arrangements of user interface 78 may be possible as well. User interface 78 may also show some elements in color if display 34 supports a color screen. In alternative embodiments, arrows 98 may not appear on user interface 78, and patient 12 may simply use control pad 28 to navigate between screens.

Figure 7:
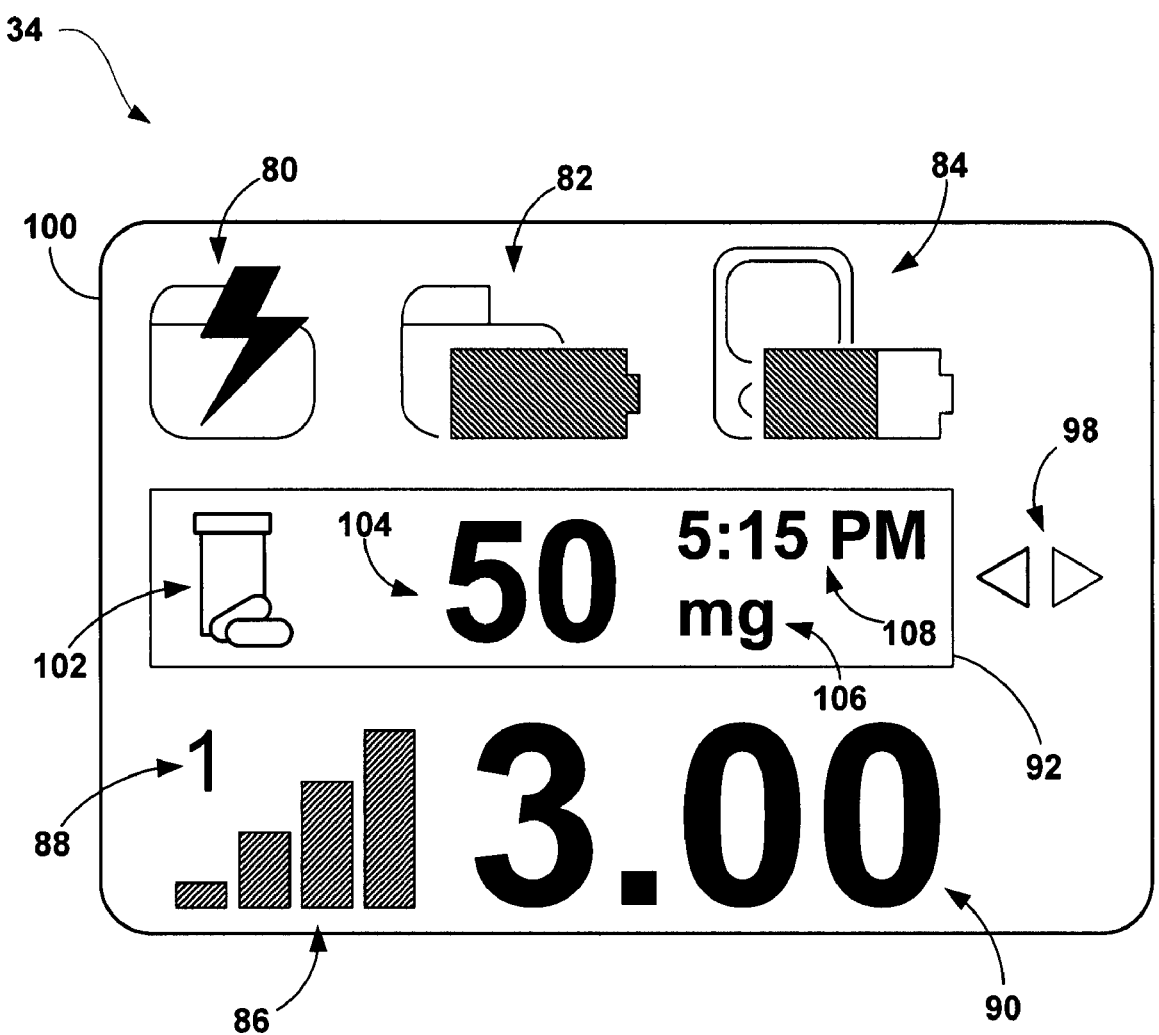
FIG. 7 is an example user interface for receiving medication dosage information from the patient as performance feedback.

FIG. 7 is an example user interface for receiving medication dosage information from the patient. In the example of FIG. 7, display 34 of programmer 20 provides user interface 100 to the user, such as patient 12. User interface 100 includes program number 88, parameter icon 86, information box 92, voltage amplitude 90, navigation arrows 98, stimulation icon 80, battery icon 84, and programmer battery 84, similar to user interface 78 of FIG. 6. User interface 100 provides information to patient 12 regarding stimulation status and medication taken by the patient. More or less information may be provided to patient 12, as desired by the clinician or patient. Increased medication may indicate more adverse effects perceived by patient 12 and less effective treatment, for example.

Information box 92 contains information regarding the medication being taken by patient 12, wherein the medication may be an example of performance feedback. In the example of FIG. 7, information box 92 displays the amount or dosage of medication currently taken as provided by patient 12. Medication icon 102 indicates to the user that information box 92 is ready to accept medication input and show the input to patient 12. Information box 92 is configured to accept medication input that corresponds to each instance patient 12 takes a dose of medication for symptoms, such as pain or movement disorders symptoms. In order words, patient 12 must provide feedback to programmer 20 for each time during the day that medication is taken.

Dosage 104 indicates the volume or weight of medication just taken by patient 12. Units 106 indicate the units of dosage 104. As shown in FIG. 7, patient 12 has entered a medication input of 50 milligrams (mg). Patient 12 may use pad 28 to increase or decrease dosage 104 until the dosage matches the amount of drug taken by the patient. Patient 12 may also adjust units 106 to match the drug. For example, patient 12 may select grams (g) or milliliters (mL) depending on the dosage. In addition, timestamp 108 indicates to patient 12 the current time of day that programmer 20 will log with the medication input. In alternative examples, patient 12 may be able to adjust timestamp 108 to correctly indicate the exact time medication was taken by the patient. In some examples, the dosage of medication remains the same for patient 12. In this case, patient 12 may review information box 92 and enter the same information each time pain medication is taken.

Programmer 20 may associate the medication input with a single drug that patient 12 takes for symptom management. In some examples, user interface 100 may allow patient 12 to select which type of drug was just taken when the patient takes multiple medications. Programmer 20 may estimate or determine the condition of patient 12 based upon the dosage and type of drug patient 12 has taken to help reduce symptoms not managed by the stimulation therapy, or counteract negative effects of the stimulation therapy. Programmer 20 may include a lookup table or set of equations for determining the magnitude of symptoms, e.g., pain or movement disorder symptoms, or adverse effects of stimulation, based upon the strength and dosage of medication taken by patient 12. Programmer 20 may determine stimulation performance, e.g., percent changes in efficacy or adverse effects, based on changes in the magnitude of symptoms or adverse effects as determined using such lookup tables or equations.

In alternative examples, patient 12 may not need to provide medication input every time that medication was taken. Patient 12 may create many medication inputs at the end of each day to approximate how much medication was taken. In this case, patient 12 may not be burdened by continuous logging of medication. Programmer 20 may provide daily, weekly, or monthly graphs of medication taken by patient 12 so that the patient can review trends in stimulation therapy efficacy. Patient 12 may use arrows 98 or pad 28 to scroll through recent medication inputs.

Figures 8A, 8B:
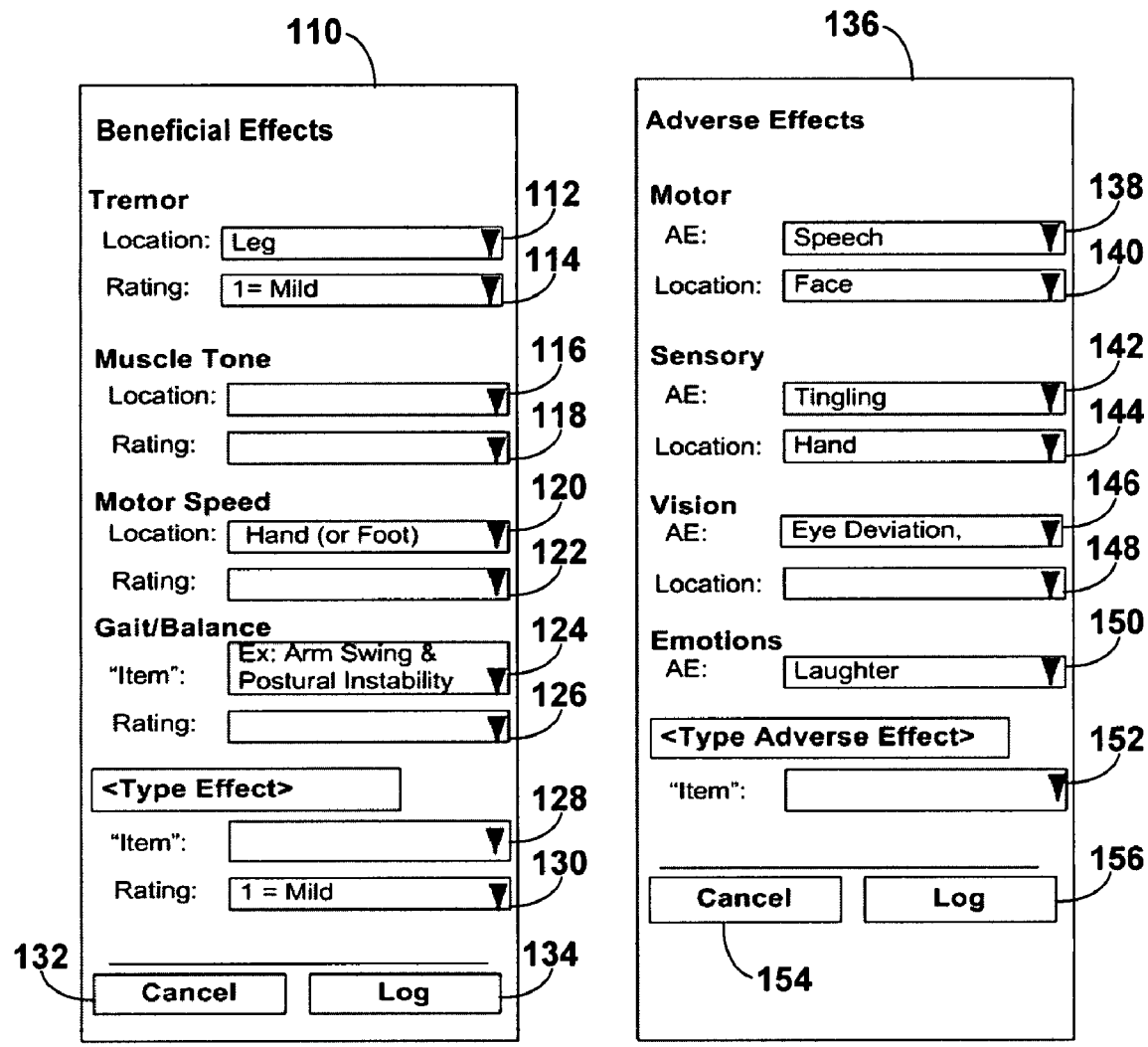
FIGS. 8A and 8B are illustrations of example user interfaces for receiving performance feedback in the form of beneficial effects and adverse effects.

FIGS. 8A and 8B are illustrations of example user interfaces for receiving performance feedback in the form of beneficial effects and adverse effects. While FIGS. 8A and 8B are described for use in a clinician programmer, the user interfaces may also be implemented in a programmer used by a patient, or some other computing device. FIG. 8A is an example screen illustrating drop-down menus for rating beneficial effects of stimulation. As shown in FIG. 8A, GUI 110 pops up to allow the clinician to provide positive input rating beneficial effects associated with the therapy. Effects listed in GUI 110 may be diagnosis dependent and are presented by programmer 20 according to the diagnosis of patient 12. GUI 110 may include example effects for patient 12 diagnosed with Parkinson's disease. Other effects may be present in GUI 110 for a patient diagnosed with other diseases or conditions.

GUI 110 includes multiple categories for specific feedback input. Location menu 112 and rating menu 114 describe any tremors in terms of rating, e.g., mild, moderate, sever, and location in the patient's body, e.g., leg. Location menu 116 and rating menu 118 describe muscle tone of patient 12 in terms of rating and location in the patient's body, e.g., leg. Location menu 120 and rating menu 122 describe motor speed of patient 12 in terms of rating and location in the patient's body, e.g., hand or foot. Patient gait and balance is also described by item menu 124 and rating menu 126, e.g., arm swing and postural instability. In addition, the clinician may type in another effect not listed in GUI 110. This custom effect is described with item menu 128 and rating menu 130.

The clinician selects log button 134 to save and exit GUI 110. All beneficial effect and/or rating information is saved in memory 70 of programmer 20 and/or in memory 60 of IMD 14. Alternatively, the clinician may select cancel button 132 to avoid saving any rating information of the beneficial effects and exit GUI 110. Programmer 20 uses the rating information provided in the inputs of GUI 110 to determine the performance feedback and efficacy for the delivered therapy. In addition, programmer 20 may sort and/or weight the therapy based upon the rating information collected from the clinician with GUI 110. In some embodiments, rating information may not be used when logging the effects. Simply noting that tremors in the leg of patient 12 have been reduced may be enough information to effectively determine therapy performance and create a program path within the therapeutic tree.

FIG. 8B is an example screen illustrating drop-down menus for rating the adverse effects of stimulation. As shown in FIG. 8B, GUI 136 allows the clinician to provide adverse effects for performance feedback associated with the therapy. Adverse effects listed in GUI 136 are therapy dependent and are presented by programmer 20 according to the type of stimulation therapy provided to patient 12. GUI 110 may include example adverse effects for patient 12 being given stimulation directed to treating Parkinson's disease.

Other adverse effects may be present in GUI 136 for a patient given other stimulation therapies. GUI 136 includes multiple categories, similar to GUI 136, for specific feedback. Adverse effect (AE) menu 138 and location menu 140 describe adverse motor effects, e.g., adverse effect: speech and location: face. AE menu 142 and location menu 144 describes adverse sensory affects noticed by patient 12, e.g., adverse effect: tingling and location: hand. AE menu 146 and location menu 148 describe any adverse effects to vision, e.g., adverse effect: eye deviation, and AE menu 150 describes adverse emotional changes due to the test program, e.g., adverse effect: laughter. In addition, the clinician may type in another adverse effect not listed by GUI 136. The other adverse effect is further described with item menu 152. Further, although not illustrated in FIG. 8B, some embodiments may include alphanumerical or other types of user-entered ratings for each adverse effect. In some examples, GUIs 110 and 136 may be included in the same GUI with tabs that allow the clinician to toggle between the beneficial effects of GUI 110 and the adverse effects of GUI 136.

Similar to GUI 110, the clinician selects log button 156 to save and exit GUI 136. All effect and/or rating information is saved in memory 70 of programmer 20 and/or in memory 60 of IMD 14. Alternatively, the clinician may select cancel button 154 to avoid saving any effect or rating information and exit GUI 136.

Figure 9:
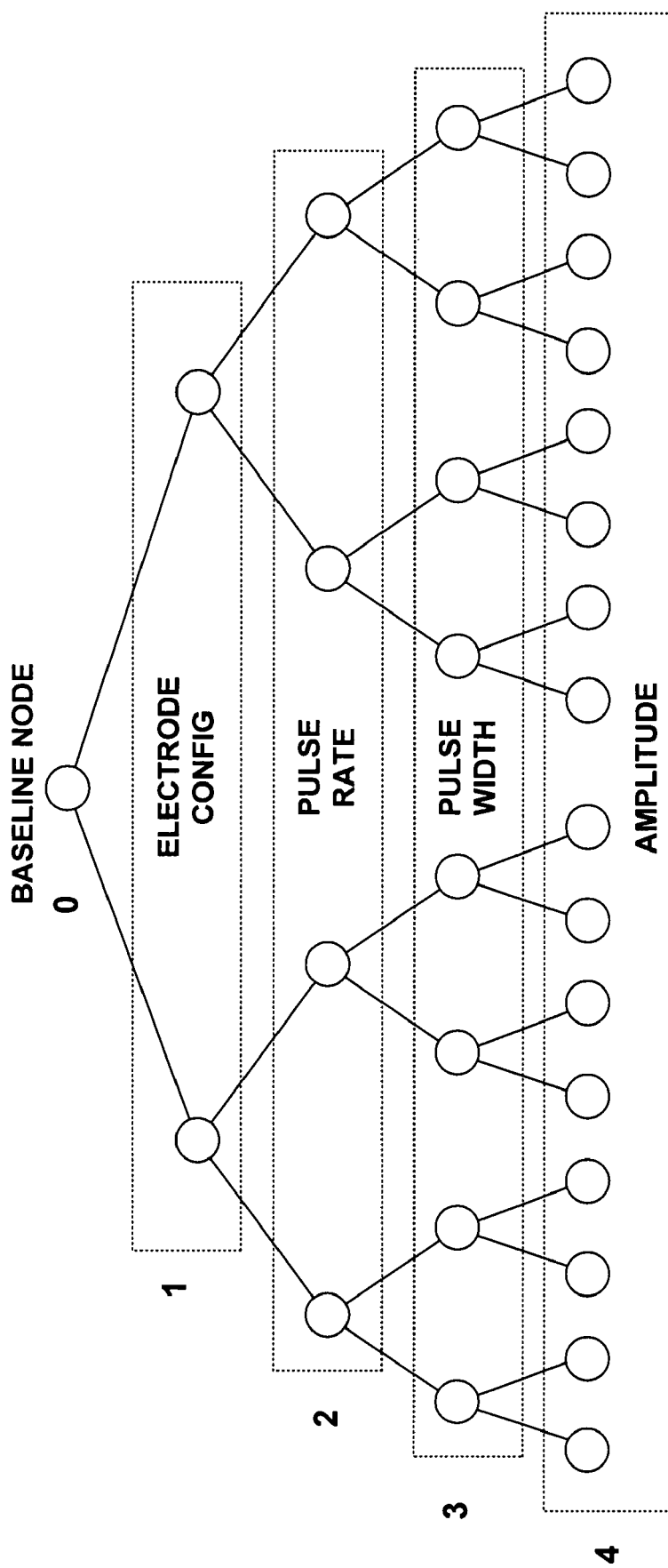
FIG. 9 is a diagram of a therapeutic tree structure for programming parameters associated with stimulation delivered by an implanted stimulator.

FIG. 9 is a diagram of a therapeutic tree structure for programming parameters associated with stimulation delivered by an implanted stimulator. As shown in FIG. 9, the therapeutic tree structure includes a baseline node, representing the baseline condition of the patient without stimulation therapy for treating pain, at a level 0 of the tree. At level 1, the tree includes two or more nodes specifying parameter sets for stimulation therapy. The parameter sets may specify electrode configurations (including combination and polarity, if applicable), pulse rate, pulse width and voltage or current amplitude. In some examples, stimulation parameters may include pulse charge density. A pulse change density may be a parameter that is similar to the combination of amplitude and pulse width, and may also consider the size of electrodes used to deliver pulses. The pulse charge density may be used in addition to or in place of the amplitude and/or pulse width parameters.

In the example of FIG. 9, the different nodes in level 1 represent identical values for pulse rate, pulse width and amplitude, but different electrode configurations. The pulse rate, pulse width and amplitude values are initial values that may be predetermined or selected by the clinician. Hence, the different nodes in level 1 represent different electrode configurations. As one example, one node may specify a combination of two electrodes as cathode and anode, while another node specifies the same combination of electrodes, but as anode and cathode. Hence, the level 1 nodes present different electrode configurations and/or polarities.

Each node in level 1 is connected to two or more nodes in level 2. Each node in level 2 has the same electrode configuration as the node to which it is connected above in level 1. In addition, the pulse width and amplitude values for the level 2 nodes may be the same as in level 1. However, in level 2, different nodes connected to the same level 1 node have different pulse rate values. Hence, level 2 represents different pulse rate adjustments to the stimulation program, given the other parameter values defined by the node above.

Each node in level 2 is connected to two or more nodes in level 3. Each node in level 3 has the same electrode configuration and pulse rate as the node to which it is connected above in level 2. In addition, the amplitude values for the level 3 nodes may be the same in level 1. In level 3, however, different nodes connected to the same level 2 node have different pulse width values. Hence, level 3 represents different pulse width adjustments to the stimulation program, given the other parameter values defined by the node above.

Each node in level 3 is connected to two or more nodes in level 4. Each node in level 4 has the same electrode configuration, pulse rate and pulse width as the node to which it is connected above in level 3. However, different nodes connected to the same level 3 node have different amplitude values. Hence, level 4 represents different amplitude adjustments to the stimulation program, given the other parameter values defined by the node above.

The physician, patient, programmer and/or stimulator travel along a path through the therapeutic tree based on performance feedback from the patient and/or clinician, sensors 63, or processor 58. For example, the clinician or patient may control the path through the tree by entering feedback information into programmer 20, in which case the programmer may select the next node in the tree, either automatically or the clinician or patient confirms the selection.

In addition, in some embodiments, programmer 20 or stimulator 14 may define the program path automatically based on feedback input received from the patient or clinician via the programmer, or performance feedback received from one or more sensors 63. In each case, relative feedback provided by stimulation parameters associated with the nodes serves to guide the program along the tree to the next node.

In the example of FIG. 9, the order of levels proceeds from electrode combination/polarity at level 1, to pulse rate at level 2, pulse width at level 3, and amplitude at level 4. Hence, the therapy parameters are prioritized such that electrode combination/polarity is used for high-level coarse tuning, as it is perceived as heavily impacting stimulation efficacy, e.g., due to it role in positioning the stimulation relative to a target tissue site.

The other parameters are prioritized in order of impact to provide progressively finer tuning of the stimulation parameter set. For example, after electrode combination/polarity, pulse rate may be viewed as having the next largest impact on performance feedback, followed by pulse width and pulse amplitude. The prioritization shown in FIG. 9 is for purposes of example, however, and should not be considered limiting of the invention. Rather, in other embodiments or implementations, the order of parameters among the hierarchy of the therapeutic tree may be subject to variation.

Although each level in the example tree of FIG. 9 represents bifurcated branching from a node above, i.e., from one node to two nodes, each node may branch to two, three, or more nodes in the next level below. In addition, although FIG. 9 shows four levels, not counting the baseline node, additional levels may be added to the tree for additional stimulation parameters or to permit more fine tuning of any of the parameters adjusted in the levels above. Accordingly, the tree in FIG. 9 is provided for purposes of illustration, and may be simpler or more complex for a given stimulation pain therapy implementation.

Furthermore, the tree structure may be created or modified based on user input or other considerations, which may be specific to a patient, therapy, or stimulator or lead configuration. For example, the range of parameter values in each level may be configured based on the limitations of a system 10, or based on patient comfort and safety considerations. Available stimulation amplitudes, for example, may be limited based on considerations such as size of electrodes and charge density.

The therapeutic tree may also be used to create new programs from existing programs. In this manner, programs created with the therapeutic tree may be grouped together according to their use, such as the time of day, posture, activity, or other circumstance where a variation in stimulation between the grouped programs may provide improved therapy for patient 12. For example, any new program created from an existing program with the therapeutic tree may be grouped with the existing program. Alternatively, a new program may be added to a current group by using the therapeutic tree; however, the therapeutic tree may eliminate any parameters that have been found to be ineffective with other programs associated with that specific group of programs. In this manner, the user may more quickly create programs directed to a group of programs. Also, as indicated above, nodes of the therapeutic tree may include power usage values or other aspects of stimulation that the clinician desires to use as performance feedback to create a program path.

Figure 10:
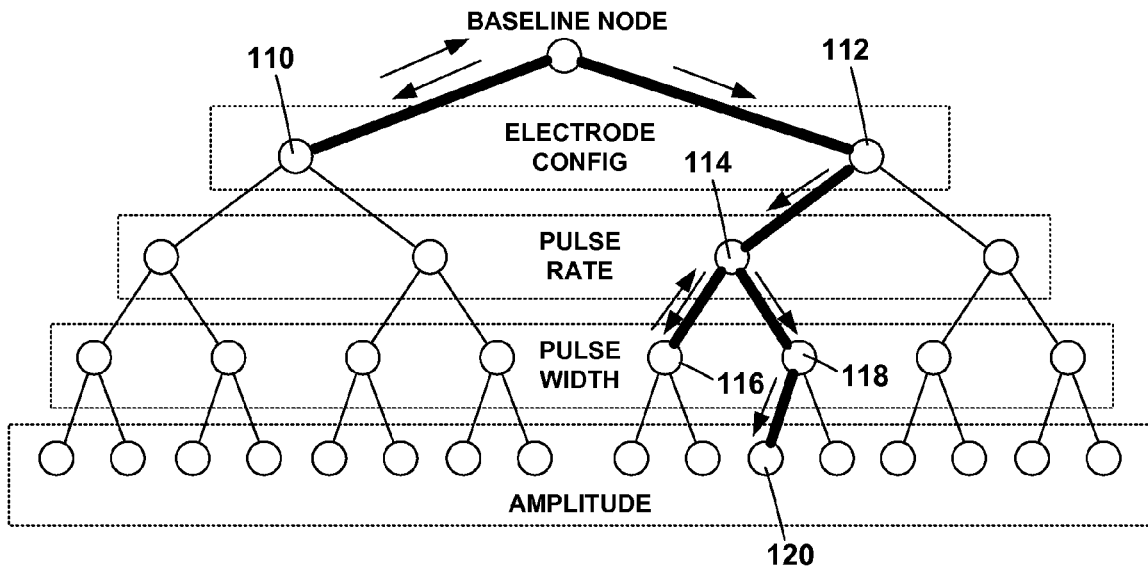
FIG. 10 is a diagram illustrating traversal of the therapeutic tree to define an example program path.

FIG. 10 is a diagram illustrating traversal of the therapeutic tree to define an example program path. As shown in FIG. 10, the program path first traverses from the baseline node downward to a first node 110 in level 1, which defines a particular electrode combination and/or polarity. In this example, the performance improvement produced by node 110 relative to the patient's baseline condition, i.e., without therapy, is less than a specified threshold level, e.g., 50%. Accordingly, the program path progresses no further down the path connected to node 110, and instead reverses through the baseline node to the second node 112 at level 1. In this case, node 112 presents a performance improvement in excess of 50%, and the program path proceeds to the next node 114, which resides in level 2 and specifies a change in pulse rate, while maintaining the electrode configuration and other parameters of node 112.

The threshold level that patient 12 uses to determine the performance of a program may depend upon the baseline pain or movement disorder symptoms perceived by the patient compared to a completely treated condition. A therapy that reaches a 50 percent efficacy threshold may successfully make patient 12 feel like half of the symptoms are gone while half of the symptoms are still perceived. For example, patient 12 may use a symptom scale that ranges from 1 to 10, where 10 indicates that the symptoms are unbearable and 1 indicates a symptom free or normal condition. Patient 12 may indicate that their untreated baseline condition is an 8. For the program to provide 50 percent efficacy, patient 12 would need to indicate a condition of 4 on the 1 to 10 scale. Alternatively, patient 12 may indicate two smile icons 96 out of four smile icons in user interface 78 of FIG. 6. In other examples, the 50 percent threshold may apply to 50 percent fewer sleep interruptions during the night or being able to stand for 50 percent greater amount of time. The thresholds for performance feedback may be different according to the type of stimulation therapy, patient condition, or patient desires.

Node 114 defines stimulation parameters that are found to yield a feedback improvement in excess of 50%. As a result, the program path continues along a path connected to node 114. In particular, the program path first evaluates parameters associated with node 116 in level 3. Node 116 represents an adjustment to pulse width, while maintaining the electrode configuration and pulse rate specified by node 114. However, the performance feedback reveals that node 116 does not achieve an feedback improvement of greater than 50%. For this reason, the program path returns to node 114 and traverses another branch of node 114 to node 118.

At node 118, the stimulation parameters produce a feedback improvement in excess of 50% relative to the baseline condition of the patient. In response, the program path proceeds to node 120 in level 4, which represents a change in amplitude but otherwise maintains the parameter values associated with node 118 in level 3. Generally, a 50 percent feedback improvement relative the baseline patient condition is required to continue along a path extending from a particular node. However, once a program path reaches the bottom of the tree, e.g., level 4, additional program paths may still be created until a higher percent efficacy is reached, e.g., 80%.

Once patient 12 is experiencing an 80 percent feedback improvement relative to the baseline condition along a given program path, the process may be terminated at the current node in that program path or the process may only proceed to fine tune parameters using lower levels along the same path. As mentioned previously, the 50% and 80% feedback thresholds are only examples, and the clinician may utilize thresholds that are any percentage. Further, representations or measures of performance feedback or feedback improvement other than percentages may be used in some embodiments.

Figure 11:
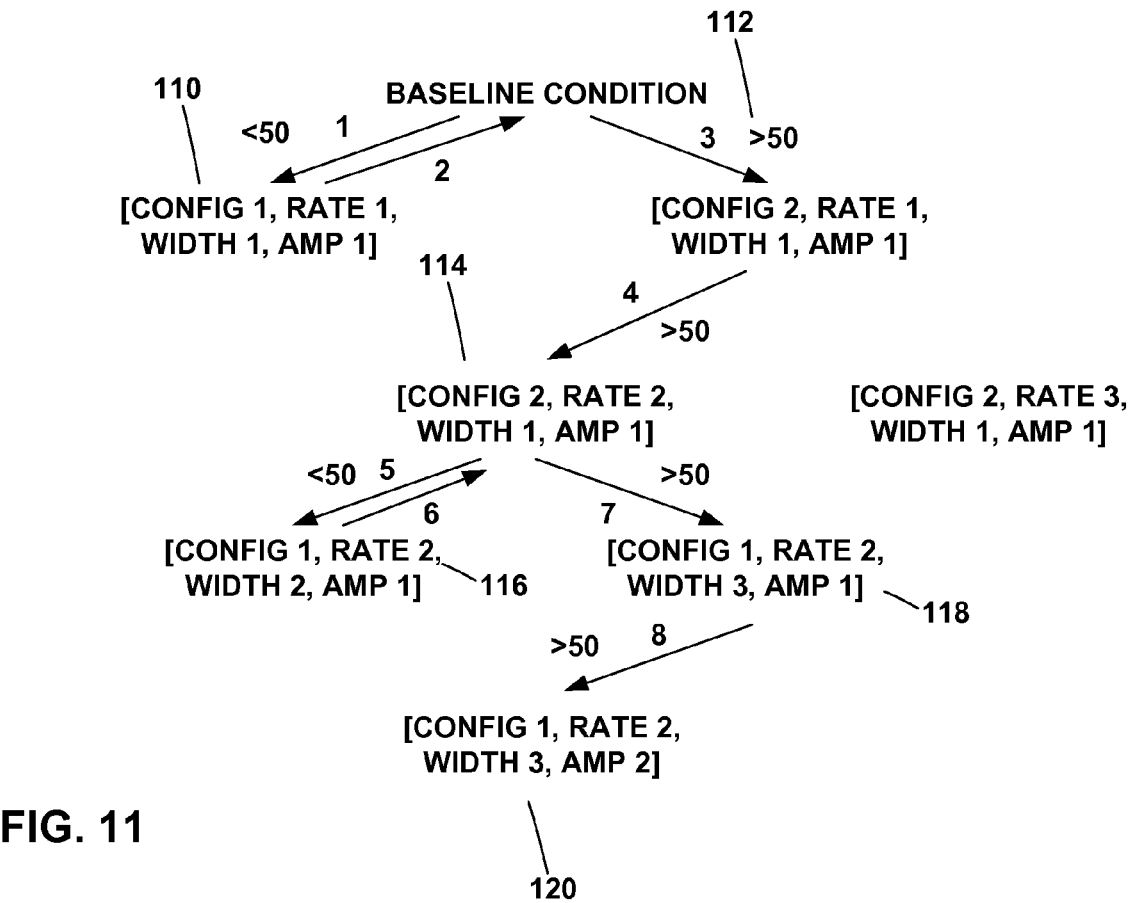
FIG. 11 is a diagram illustrating the program path of FIG. 9 in terms of parameter sets associated with nodes in the program path.

FIG. 11 is a diagram illustrating the program path of FIG. 10 in terms of parameter sets associated with nodes in the program path for stimulation pain therapy. In particular, FIG. 11 shows parameter sets corresponding to nodes 110, 112, 114, 116, 118 and 120 of FIG. 10. In addition, FIG. 11 numbers the steps along the program path as steps 1, 2, 3, 4, 5, 6, 7, and 8. As shown, nodes 110 and 112 include similar parameter sets but different electrode configurations. In particular, node 110 specifies [Config 1, Rate 1, Width 1, Amp 1] and node 112 specifies [Config 2, Rate 1, Width 1, Amp 1], where configuration represents electrode combination/polarity, rate represents pulse rate, width presents pulse width and amp represents amplitude. In the next level, FIG. 11 shows node 114 in terms of the parameter set [Config 2, Rate 2, Width 1, Amp 1]. In this case, the electrode configuration, pulse width and amplitude are the same as node 112 above, but Rate 2 is different from Rate 1, representing a pulse rate adjustment.

Figure 12:
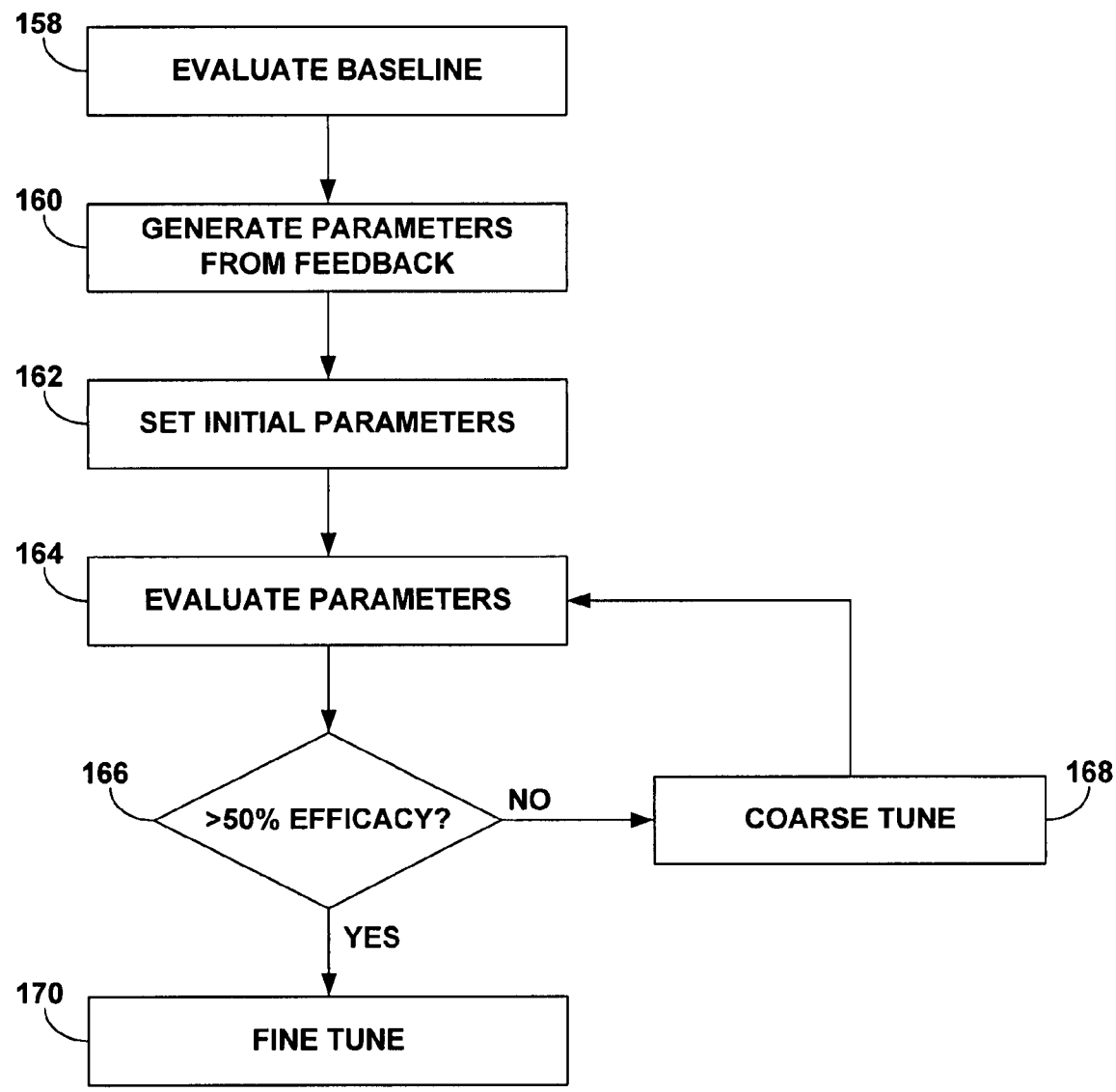
FIG. 12 is a flow chart illustrating a technique for programming the implanted stimulator.

FIG. 12 is a flow chart illustrating an example technique for programming the implanted stimulator. Although described with reference to programmer 20, the example technique may be performed by other components of systems 10, 22, such as stimulator 14.

As shown in FIG. 12, the clinician aids patient 12 in initially finding a program path to deliver stimulation therapy. First, a baseline condition, e.g., the initial condition of the patient without stimulation, is evaluated (158). Evaluating the initial condition may include providing feedback to criteria from external programmer 20 describing the severity of symptoms perceived by the patient before stimulation is applied. Evaluating the initial condition may additionally or alternatively evaluating signals from one or more physiological parameter sensors, or metrics derived from such signals.

From the baseline information, external programmer 20 generates initial parameters to begin stimulation therapy (160). The initial parameters may be specified or approved by the clinician. At this point in the process, the therapeutic tree has not yet been used. The clinician uses external programmer 20 to begin initial stimulation (162) to evaluate nodes in the therapeutic tree.

The stimulation therapy from the initial parameters is evaluated (164). In some cases, the therapy may have to be evaluates over a long period of time, such as 24 hours or more. If the feedback from patient 12 or sensors 63 indicates that the initial stimulation therapy is approximately greater than a 50% improvement (166) relative to the baseline condition, external programmer 20 moves directly into fine tuning, i.e., by moving to a lower level of the therapeutic tree (170). If the therapy is less than 50 percent effective (166), external programmer 20 moves to gross or coarse tune by moving to another node of the first level of the therapeutic tree to more coarsely change the stimulation therapy (168). Then, patient 12 evaluates the new parameters of the coarse tune (168). Fine tuning further follows the therapeutic tree and is described in FIG. 13.

Feedback from patient 12 or the clinician may be in the form of feedback input related to the ability of the stimulation to reduce symptoms, extent of adverse side effects resulting from the stimulation, medication input, power consumption associated with stimulation, or any combination thereof. Initially, the program path of the therapeutic tree may be created through feedback input. Feedback input may additionally or alternatively include sensor-based feedback reflecting how much the pain has been reduced through stimulation.

Figure 13:
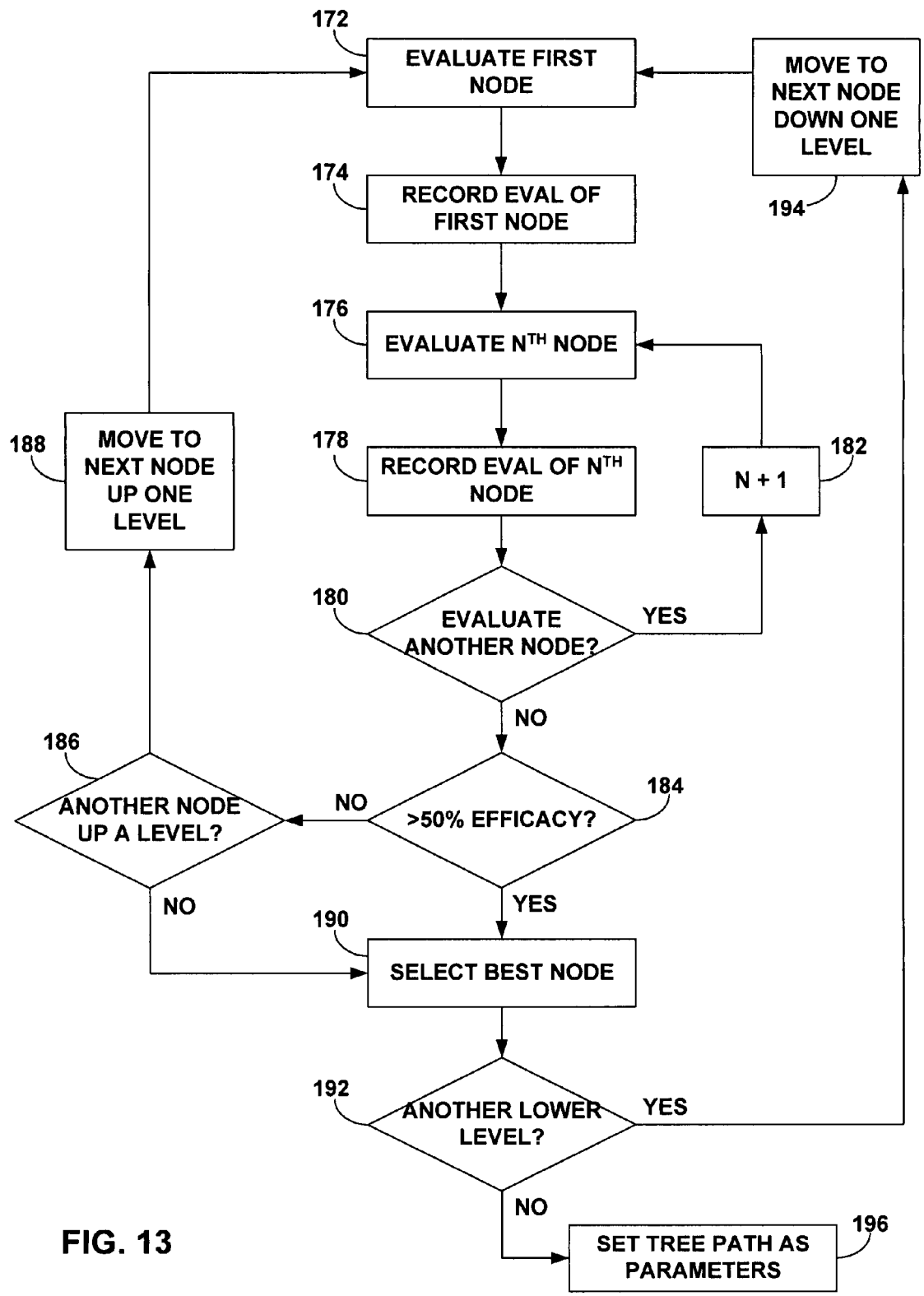
FIG. 13 is a flow chart illustrating a technique for fine tuning the programming of the implanted stimulator.

FIG. 13 is a flow chart illustrating a technique for fine tuning the programming of the implanted stimulator 14. Although described with reference to programmer 20, the example technique may be performed by other components of systems 10, 22, such as stimulator 14. Furthermore, although described in the context of patient input as performance feedback, the technique may additionally or alternatively be practiced with sensor signals, or values derived therefrom, as the performance feedback.

As shown in FIG. 13, the therapeutic tree is used to fine tune stimulation therapy by creating a program path to best treat the symptoms of patient 12. The patient first evaluates the first node of the second level (172). Patient 12 records the evaluation of the first node using programmer 20 (174). Next, patient 12 evaluates the Nth node (176) and the patient records the evaluation of the Nth node (178). If there is another node of the second level to evaluate (180), programmer 20 adds 1 to the Nth node (182) and patient 12 evaluates the N+1 node (176). If there is no other node to evaluate, programmer 20 determines if any of the evaluated nodes reached greater than 50 percent performance (184).

If no nodes of the second level provide greater than 50 percent efficacy, external programmer 20 checks if there is a level up one level from the current position on the therapeutic tree (186). If there is another level, programmer 20 moves up one level (188) and patient 12 evaluates another node of that upper level (172). If there is no level higher up the tree (186) or one of the evaluated nodes is greater than 50 percent effective (184), external programmer 20 selects the best node (180).

If there is a lower lever on the therapeutic tree (192), programmer 20 moves to the lower level, i.e. the third level in this example (194), and another node of the third level is evaluated (172). If there are no lower levels on the therapeutic tree to evaluate (192), programmer 20 sets the current program path as the nodes, or stimulation parameters, to deliver stimulation therapy to patient 12 (196).

In alternative examples, programmer 20 may select the best node evaluated and move down a level if no nodes provided a performance rate greater than 50 percent effective. It may be possible that parameters of lower levers can create a program that elicits a better than 50 percent performance feedback or efficacy. In other examples, such as trial stimulation, programmer 20 may quit evaluation with the therapeutic tree once therapy efficacy reaches 50 percent to save programming time. As mentioned previously, alternative performance thresholds may be selected by patient 12 or the clinician.

Also, further fine tuning steps may be performed after reaching a performance threshold or a lowest level in the tree. For example, a stimulator or programmer may be programmed, based on knowledge of nerve activation curves, to further fine tune a desirable programming path by adjusting amplitude and pulse width in concert to continue activating the same nerves. Although activating the same nerves, such adjustments may result in improved comfort, e.g., reduced side effects such as numbness, tingling, jolting with movement, nausea, slurred speech, impaired gate, or the like.

Similar to FIG. 12, feedback from patient 12 or the clinician may be in the form of feedback input related to the ability of the stimulation to reduce symptoms, medication input, or both. Initially, the program path of the therapeutic tree may be created through feedback input. Feedback input may include how much the symptoms have been reduced in one or more postures or activities or which activities are enabled by reducing symptoms through stimulation. However, programmer 20 may be capable of incorporating medication input in order to create the best program path according to all feedback related to the condition of patient 12.

Figure 14:
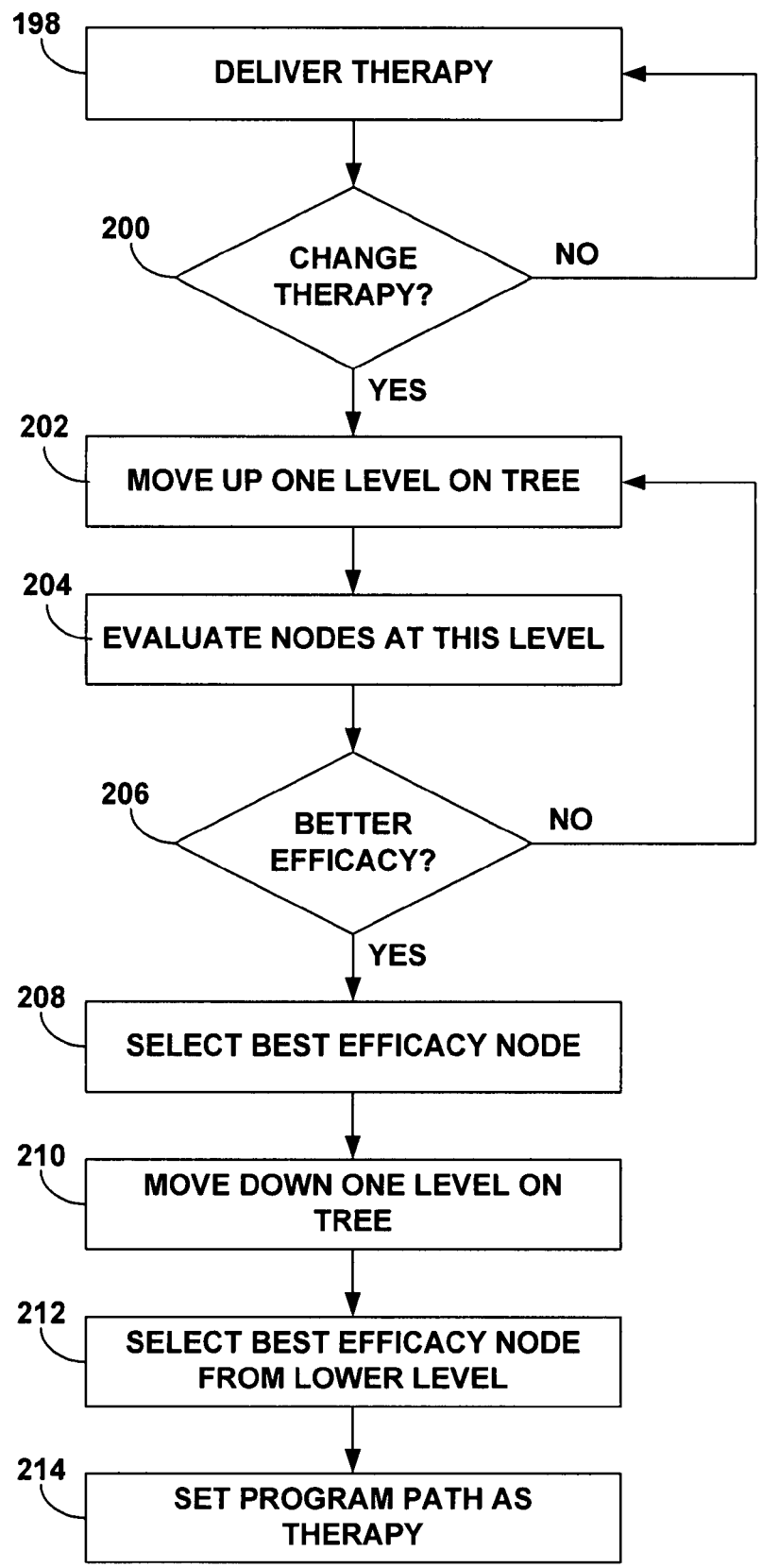
FIG. 14 is a flow chart illustrating a technique for fine tuning stimulation therapy during therapy delivery.

FIG. 14 is a flow chart illustrating a technique for fine tuning stimulation therapy during chronic therapy delivery. Although described with reference to programmer 20, the example technique may be performed by other components of systems 10, 22, such as stimulator 14. Furthermore, although described in the context of patient input as performance feedback, the technique may additionally or alternatively be practiced with sensor signals, or values derived therefrom, as the performance feedback.

As shown in FIG. 14, the program path that defines stimulation therapy may be modified during therapy. Stimulator 14 delivers therapy to patient 12 (198), and if there is no indication to change therapy (200), therapy continues unchanged. The indication to change therapy may be from stimulator 14, patient 12, or the clinician. The indication may be direct parameter change input from patient 12, a change in feedback input, or a change in sensor or medication based feedback. The amount of change that triggers the use of the therapeutic tree may be predefined or selected by patient 12 or the clinician. For example, therapy efficacy may need to drop by 10 percent or more to change the program by using the therapeutic tree. If therapy should change (200), programmer 20 moves up one level on the therapeutic tree (202). Patient 12 evaluates the nodes at this level (204) such that programmer 20 may determine if any nodes provide better performance feedback (206). If no nodes provide better efficacy, programmer 20 moves up one more level on the therapeutic tree (202).

If at least one evaluated node provides better efficacy (206), programmer 20 selects the best efficacy node based upon patient 12 feedback (208). Programmer 20 moves down one level on the therapeutic tree from the selected node (210) and programmer 20 selects the best efficacy based upon the additional performance feedback (212). Programmer 20 sets the program path as the stimulation parameters for therapy and delivers the stimulation to patient 12 (214).

Similar to FIG. 12, feedback from patient 12 or the clinician may be in the form of feedback input related to the ability of the stimulation to reduce symptoms, medication input, or both. Initially, the program path of the therapeutic tree may be created through feedback input. Feedback input may include who much the symptoms have been reduced in one or more postures or activities or which activities are enabled by reducing symptoms through stimulation. However, programmer 20 may be capable of incorporating medication input in order to create the best program path according to all feedback related to the condition of patient 12.

Figure 15:
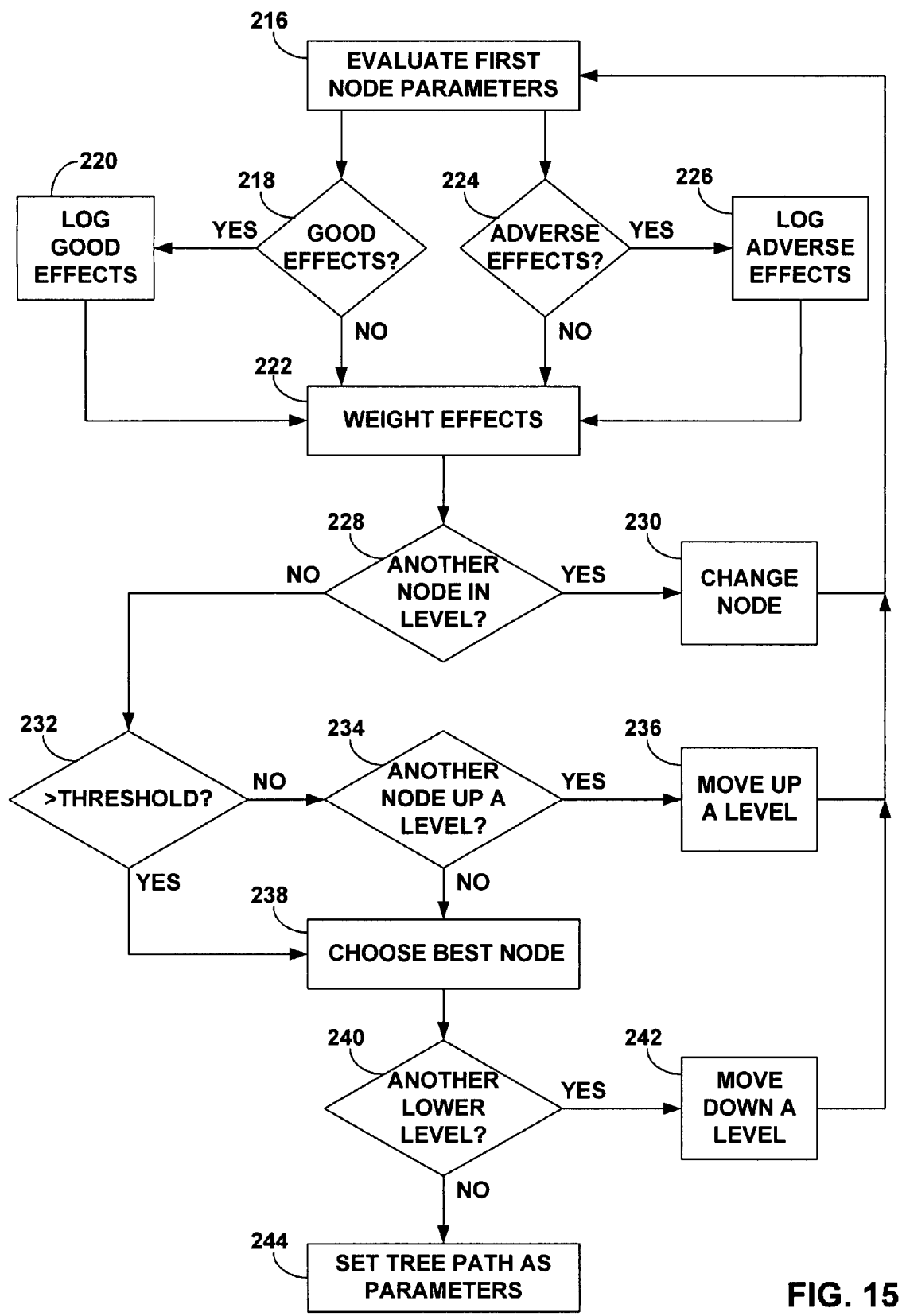
FIG. 15 is a flow chart illustrating a technique for fine tuning the programming of the implanted stimulator with weighted beneficial effects and adverse effects.

FIG. 15 is a flow chart illustrating a technique for fine tuning the programming of the implanted stimulator with weighted beneficial effects and adverse effects. Although described with reference to programmer 20, the example technique may be performed by other components of systems 10, 22, such as stimulator 14. Furthermore, although described in the context of patient input as performance feedback, the technique may additionally or alternatively be practiced with sensor signals, values derived therefrom, or processor calculated values as the performance feedback. As shown in FIG. 15, the therapeutic tree is used to fine tune stimulation therapy by creating a program path to best treat the symptoms of patient 12. The patient first evaluates the first node of the second level (216). If the patient perceives beneficial effects (218), programmer 20 prompts the user to log the beneficial effects (220). If the patient perceives adverse effects (224), programmer 20 prompts the user to log the adverse effects (226).

After the user logs effects from the therapy, the effects may be weighted in order to optimize the selection of nodes (222). Weighting may be performed to place greater importance on some effects and less importance on other effects. For example, reducing adverse effects may be of higher priority to therapy efficacy. Therefore, adverse effects may be weighted greater than beneficial effects. The weighting may be determined by the manufacturer, the clinician, patient 12, or any combination thereof.

Additionally, different beneficial effects or adverse effects may be weighted differently than other beneficial effects or adverse effects, respectively. For example, if an occupation or hobby of a patient makes avoidance of a particular adverse effect, such as slurred speech, paramount, that adverse effect may be weighted more heavily than others. As an example, beneficial and adverse effects may be given positive and negative weights, respectively, and then summed. The magnitude weights may be retrieved from a look-up table, and may be determined based on user prioritization. In some cases, the weights may be multiplied by a rating number that indicates the intensity or extent of the effect prior to the summation. Such rating numbers are discussed above with reference to FIGS. 8A and 8B.

If there is another node in the current level of the therapeutic tree (228), programmer 20 may change to another node (230) and continue evaluating the new node parameters (216). If there is no other node in the current level of the therapeutic tree (228), programmer 20 checks to see if any of the nodes provided greater than a threshold level of performance, e.g., based on comparison of the weighted sum to a threshold value (232). If one node provided better than the threshold performance (232), programmer 20 chooses the best node and proceeds (238). If no node provided better than the threshold performance (232), programmer 20 checks if there is another node in a level higher (234). If there is another node, programmer 20 moves up a level (236) and evaluates a new node in the higher level (216). If there is no other node in a higher level (234), programmer 20 chooses the best node evaluated (238).

If there is a lower level left in the therapeutic tree (240), programmer 20 moves down a level (242) and continues to evaluate new nodes (216). If there is no lower level in the tree (240), programmer 20 sets the current tree path as the stimulation parameters and delivers therapy (244). In cases where other system performance values were used to select nodes and efficacy was not acceptable, system performance values may be discarded in order to select a program path through the therapeutic tree that provides efficacious stimulation therapy.

In alternative examples, programmer 20 may select the best node evaluated and move down a level if no nodes provided an efficacy greater than the threshold performance. It may be possible that parameters of lower levels can create a program that elicits a better than the threshold performance. In other examples, such as trial stimulation, programmer 20 may quit evaluation with the therapeutic tree once therapy performance reaches the threshold to save programming time.

Although not discussed in the example of FIG. 15, stimulation system performance values, e.g., power consumption values, may be considered as feedback in a weighted combination with beneficial and adverse effects. Power consumption may be actual, e.g., based on current drain or other measurements, or estimated based on the current stimulation parameters.

Similar to FIG. 12, feedback from patient 12 or the clinician may be in the form of feedback input related to the ability of the stimulation to reduce symptoms, medication input, or both. Initially, the program path of the therapeutic tree may be created through feedback input. Feedback input may include how much the symptoms have been reduced in one or more postures or activities or which activities are enabled by reducing symptoms through stimulation. However, programmer 20 may be capable of incorporating medication input in order to create the best program path according to all feedback related to the condition of patient 12

Furthermore, medication input may be used to indicate how often to revisit the therapeutic tree structure for reprogramming. For example, to the extent that the patient is given some control of dosage amount or frequency, increases in these values may indicate a need to reprogram stimulation therapy for improved efficacy. Additionally, the extent of use or medication may color the any subjective evaluation of efficacy. For example, subjective efficacy indications may be weighted based on whether the patient's condition was also being alleviated by a drug therapy at the same time. Also, patient input on medication use may impact the time between evaluations of new branches on the tree. For example, a programmer or stimulator may wait until a medication dose is effective, or has run its course, to try a new programming path in the tree structure.

Figure 16:
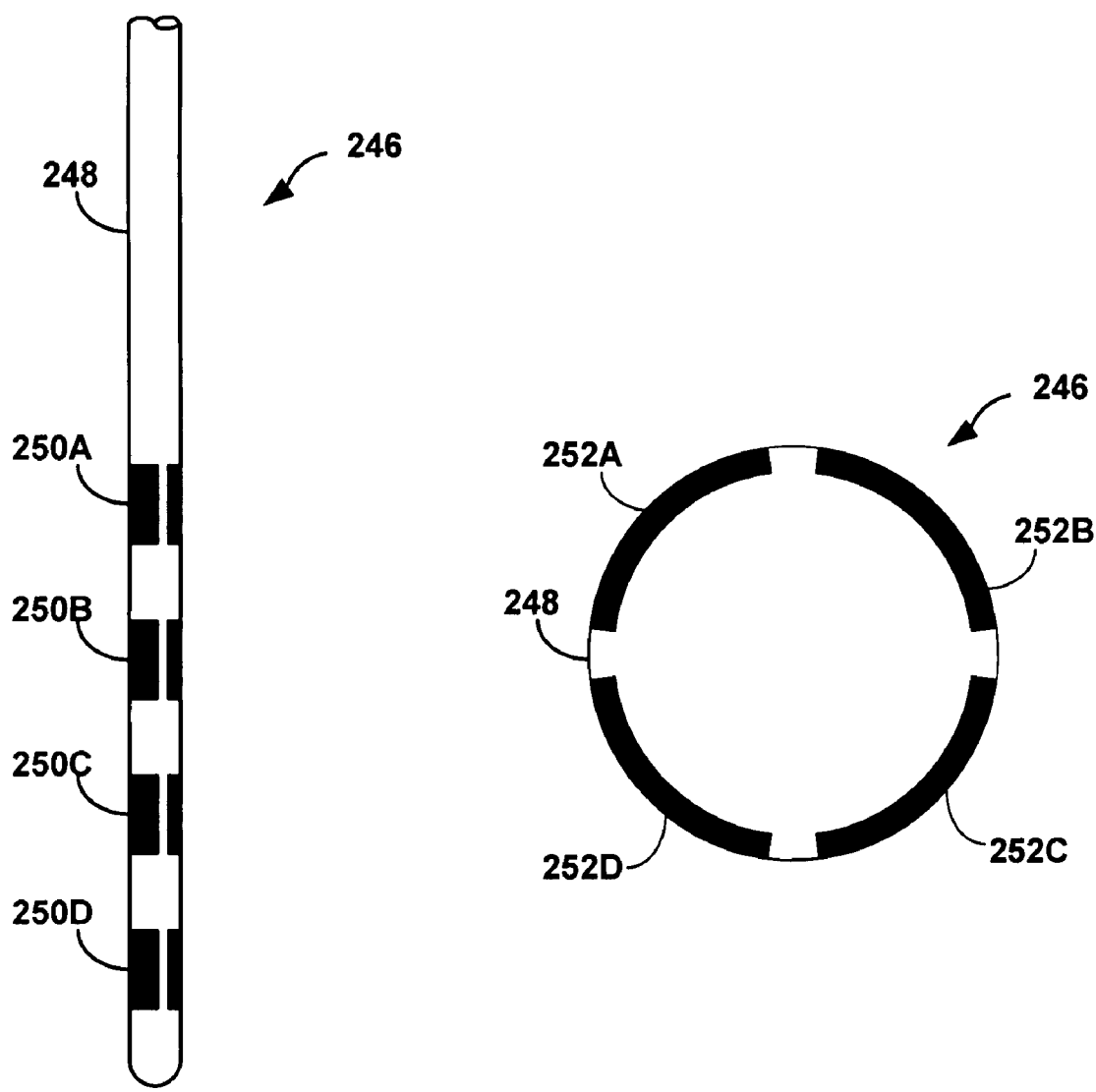
FIGS. 16A and 16B are conceptual illustrations of an example complex electrode array geometry for delivering stimulation therapy to a patient.

FIGS. 16A and 16B are conceptual illustrations of an example complex electrode array geometry for delivering stimulation therapy to a patient. As shown in FIG. 16A, lead 246 is an embodiment of leads 16 of FIG. 1 or leads 28 of FIG. 2. Lead 28 will be used as an example in FIGS. 16A and 16B. As shown in FIG. 16A, lead 246 includes four electrode levels 250 (includes levels 250A-250D) mounted at various lengths of lead housing 248. As an example, lead 246 may is inserted into through head 24 to a target position within brain 25. Lead 246 is an example of a complex electrode array geometry.

Lead 246 is implanted at a location determined by the clinician to be near an anatomical region to be stimulated. Electrode levels 250 are equally spaced along the axial length of lead housing 248 at different axial positions. Each electrode level 250 may have two or more electrodes located at different angular, or perimeter, positions around the circumference of lead housing 248. Electrodes may be partial ring electrodes, segmented electrodes, or other individually spaced electrodes. Electrodes of one circumferential location may be lined up on an axis parallel to the longitudinal axis of lead 246. Alternatively, electrodes of different electrode levels may be staggered around the circumference of lead housing 246. In addition, lead 246 may include asymmetrical electrode locations around the circumference of each lead or electrodes of the same level that have different sizes. These electrodes may include semi-circular electrodes that may or may not be circumferentially aligned between electrode levels. Alternatively, the individual electrodes may have alternative shapes, e.g., circular, oval, triangular, or the like.

In alternative embodiments, electrode levels 250 are not evenly spaced along the longitudinal axis of lead 246. For example, electrode levels 250A and 250B may be spaced approximately 3 millimeters (mm) apart while electrodes 250C and 250D are 10 mm apart. Variable spaced electrode levels may be useful in reaching target anatomical regions deep within brain 25 while avoiding potentially dangerous anatomical regions. Further, the electrodes in adjacent levels need not be aligned in the direction as the longitudinal axis of the lead, and instead may be oriented diagonally with respect to the longitudinal axis.

Lead housing 246 may include a radiopaque stripe (not shown) along the outside of the lead housing. The radiopaque stripe corresponds to a certain circumferential location that allows lead 246 to the imaged when implanted in patient 12. Using the images of patient 12, the clinician can use the radiopaque stripe as a marker for the exact orientation of lead 26 within the brain of patient 12. Orientation of lead 246 may be needed to easily program the stimulation parameters by generating the correct electrode configuration to match the desired stimulation defined by the clinician. In other embodiments, a marking mechanism other than a radiopaque stripe may be used to identify the orientation of lead 14. These marking mechanisms may include something similar to a tab, detent, or other structure on the outside of lead housing 248. In some embodiments, the clinician may note the position of markings along a lead wire during implantation to determine the orientation of lead 27 within patient 12.

Lead 246 may be substantially rigid to prevent the implanted lead from varying from the expected lead shape. In addition, lead 246 may be substantially cylindrical in shape. In other embodiments, lead 246 may be shaped differently than a cylinder. For example, the leads may include one or more curves to reach target anatomical regions of brain 18. In some embodiments, lead 246 may be similar to a flat paddle lead or a conformable lead shaped for patient 12. Also, in other embodiments, lead 246 may any of a variety of different polygonal cross sections taken transverse to the longitudinal axis of the lead.

FIG. 16B shows a cross-section of electrode level 250A of lead 246 which includes four electrodes 252A, 252B, 252C, and 252D (collectively "electrodes 252"). Each of electrodes 252 covers approximately 80 degrees of the circumference with approximately 10 degrees of insulation space between adjacent electrodes. In other embodiments, up to ten or more electrodes may be included within an electrode level. In alternative embodiments, consecutive electrode levels of lead 246 may include a variety of electrodes. For example, lead 246 may include electrode numbers that alternate between electrode levels 250. In this manner, various stimulation field shapes may be produced within brain 25 of patient 12. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. Smaller insulation spaces may allow a greater volume of tissue to be stimulated. In alternative embodiments, electrode size may be varied around the circumference of an electrode level. In addition, insulation spaces may vary in size as well. Such asymmetrical electrode levels may be used in leads implanted at tissues needing certain shaped stimulation fields.

Figure 17:
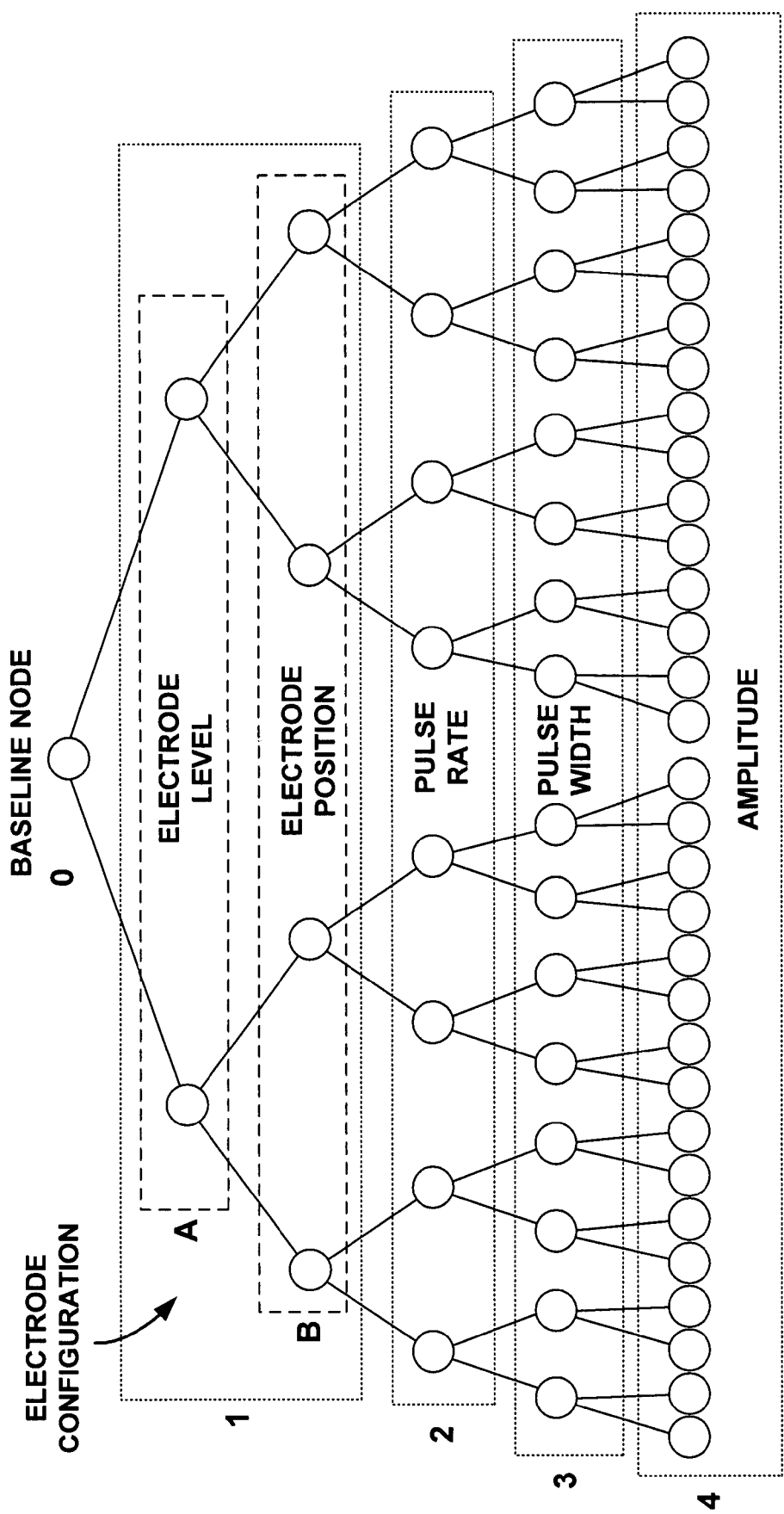
FIG. 17 is a diagram of a therapeutic tree structure for programming parameters associated with stimulation delivered by an implanted stimulator via a complex electrode array geometry.

FIG. 17 is a diagram of a therapeutic tree structure for programming parameters associated with stimulation delivered by an implanted stimulator and a complex electrode array geometry. The therapeutic tree of FIG. 17 may be substantially similar to the therapeutic tree of FIG. 9. As shown in FIG. 17, the therapeutic tree structure includes a baseline node, representing the baseline condition of the patient without stimulation therapy for treating symptoms, at a level 0 of the tree. At level 1, the tree includes two or more nodes specifying parameter sets for stimulation therapy. The parameter sets may specify electrode configurations (including combination and polarity, if applicable), pulse rate, pulse width and voltage or current amplitude.

In the example of FIG. 17, the different nodes in level 1 represent identical values for pulse rate, pulse width and amplitude, but different electrode configurations. Specifically, level one includes two sublevels A and B to identify different aspects of the electrode configuration. The pulse rate, pulse width and amplitude values are initial values that may be predetermined or selected by the clinician. Hence, the different nodes in level 1 represent different electrode configurations. Sublevel A may include nodes corresponding to each electrode level 250A-250D of lead 246, for example. When a node is used in sublevel A, all electrodes in the level are turned on or off together. Sublevel B may include nodes corresponding to each electrode of a given electrode level, for example, electrodes 252 of lead 246. In this manner, the user may systematically evaluate all electrode combinations of the complex electrode array geometry through the use of the therapeutic tree.

In other examples, level 1 may be split up into more than two sublevels. Depending upon the complex electrode array geometry implanted within patient 12, multiple sublevels may be beneficial in guiding the user through the therapeutic tree to create an effective program path. In alternative examples, the sublevels of level 1 may be determined by the user in order to evaluate the possible electrode configurations according to the desired stimulation therapy. The remaining levels 2-4 may be used substantially similarly to the therapeutic tree described in FIG. 9.

Figure 18:
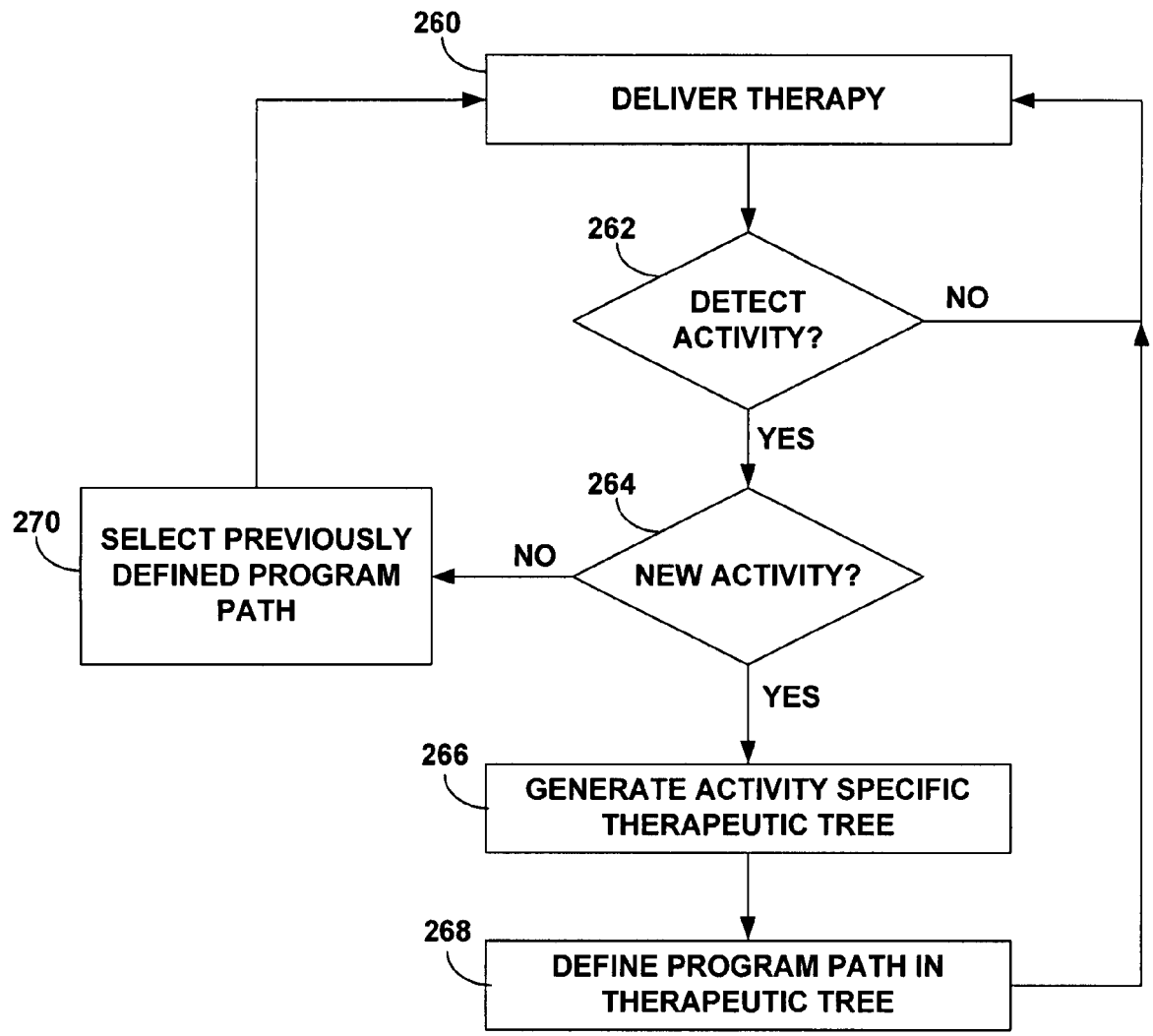
FIG. 18 is a flow chart illustrating a technique for identifying and subsequently using, for delivery of stimulation therapy, an activity-specific path in a therapeutic tree.

FIG. 18 is a flow chart illustrating a technique for identifying and using an activity-specific path through a therapeutic tree. As shown in FIG. 18, the clinician may deliver therapy to patient 12 via a program path of a therapeutic tree, e.g., a tree structure, as described above (260). However, patient 12 may benefit from a change in the stimulation therapy according to the specific activity of the patient. Therefore, a programmer or stimulator may check to see whether a particular activity undertaken by a patient has been detected (262). Example activities include, sleeping, running, golfing, swimming, speaking, or particular work or leisure related activities. The activity may be detected based on an input from a user, e.g., the clinician or patient 12, or a signal from any one or more of the sensors discussed above. For example, sleep may be detected using any of the sensors and techniques described herein, and particular physical activities may be detected based on comparison of signals from one or more accelerometers, piezoelectric elements, and/or EMG electrodes, as examples, to various thresholds or templates.

If the programmer or stimulator does not detect an activity, therapy continues as presently programmed (260). If the programmer or stimulator does detect an activity, the programmer or stimulator determines whether the activity is a new activity (264), e.g., one for which an activity-specific program path has not already been determined. If the activity is new, the programmer or stimulator may generate a therapeutic tree specific for the activity (266). For example, if the activity change indicates that patient 12 is sleeping, the activity specific therapeutic tree may be structured or weighed according to the needs of the activity. Parameters may become more or less important to therapy efficacy, or some parameter values, e.g., electrode combinations, may not be provided in the tree. Further, the thresholds used for traversing the tree may be specific to the activity. Such tree-to-tree variations may be user-configurable.

The programmer or stimulator may then define a program path through the therapeutic tree based on performance feedback received during delivery of stimulation when the patient is engaged in the detected activity (268). The defined path, e.g., the therapy parameters defined by the path, may be associated with the activity, and therapy may be delivered according to the newly defined path (260). If the activity is subsequently detected (262, 264), the stimulator or programmer may select the previously defined program path associated with the activity (270) for delivery of therapy (260).

In some embodiments, initial detecting of the activity may be based on user input. The programmer or stimulator may monitor sensor signals after receiving the user input to develop a template for subsequently detecting the activity. In other embodiments, both initial and subsequent detection of the activity may be by user input or by sensor.

The activity specific tree structure may be specific to any activity of patient 12. Example activities may include sleeping, sitting, standing, walking, running, talking, playing a sport, driving, or any other event or activity that patient 12 may participate in during the day. In some examples, programmer 20 may have activity specific tree structures preprogrammed for patient 12. In other examples, the clinician or patient 12 may need to create each activity specific tree structure as needed for therapy.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Many embodiments of the invention have been described. Various modifications may be made without departing from the scope of the claims. For example, although the invention has been generally described in conjunction with implantable stimulation devices, external stimulators, trial stimulators, drug delivery devices, or any other therapy device may be programmed through the use of a therapeutic tree and other methods described herein to treat disorders and conditions. These and other embodiments are within the scope of the following claims.

The invention claimed is:

1. A method for providing electrical stimulation therapy, the method comprising:
   defining a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, and the nodes in different levels specify adjustments to the value of different types of stimulation parameters;
   defining a program path through the tree structure along a series of the interconnected nodes for which performance feedback regarding stimulation therapy delivered according to the stimulation parameters defined by the nodes exceeds a threshold level, wherein the performance feedback comprises system performance feedback indicative of power consumption of a medical device that delivers the stimulation therapy according to the stimulation parameters defined by the selected node;
   selecting one of the nodes in the program path; and
   delivering the stimulation therapy to a patient based on the parameters defined by the selected node to treat a patient.

2. The method of claim 1, wherein the performance feedback further comprises at least one of a beneficial effect or an adverse effect.

3. The method of claim 2, further comprising weighting at least one of the beneficial effect, the adverse effect, and the system performance feedback to indicate a relative importance of at least two of the beneficial effect, the adverse effect, and the system performance feedback to define the program path.

4. The method of claim 1, wherein the system performance feedback comprises a power usage value, and wherein defining the program path through the tree further comprises selecting at least one node to minimize the power usage value.

5. The method of claim 1, wherein the stimulation therapy comprises at least one of spinal cord stimulation, deep brain stimulation, peripheral nerve stimulation, or peripheral nerve field stimulation.

6. The method of claim 1, wherein the stimulation therapy treats a movement disorder.

7. The method of claim 1, further comprising specifying which stimulation parameters are adjusted at which levels of the tree based on user input.

8. The method of claim 1, further comprising:
prompting a user to provide the performance feedback input;
receiving the performance feedback input via an external programmer; and
displaying the performance feedback input to the user.

9. The method of claim 1, further comprising receiving the performance feedback input via at least one sensor that measures a physiological parameter.

10. The method of claim 9, wherein the sensor measures at least one of a gait, a tremor, a seizure, and posture.

11. The method of claim 1, wherein the therapeutic tree comprises at least four levels.

12. The method of claim 11, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

13. The method of claim 12, wherein the first level of the tree comprises two sublevels of the tree including a first sublevel that specifies an adjustment to an electrode level of a complex electrode array geometry and a second sublevel that specifies an adjustment to an electrode perimeter position of the complex electrode array geometry.

14. The method of claim 1, wherein the stimulation parameters include stimulation electrode configuration, stimulation pulse rate, stimulation pulse width, and stimulation pulse amplitude.

15. The method of claim 1, further comprising defining the tree within an external programmer associated with an implantable electrical stimulator.

16. The method of claim 1, further comprising:
detecting an activity undertaken by the patient;
defining a program path specific to the activity through the tree structure along a series or the interconnected nodes for which performance feedback regarding stimulation therapy delivered according to the stimulation parameters defined by the nodes during the activity exceeds a threshold level;
subsequently detecting the activity; and
delivering the stimulation therapy to the patient according to the previously defined program path specific to the activity.

17. A system for providing electrical stimulation therapy, the system comprising:
a memory defining a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, and the nodes in different levels specify the adjustments to the value of different types of stimulation parameters; and
a processor configured to define a program path through the tree structure along a series of the interconnected nodes for which performance feedback regarding stimulation therapy delivered according to the stimulation parameters defined by the nodes exceeds a threshold level, selects one of the nodes in the program path, and controls delivery of the stimulation therapy to a patient based on the parameters defined by the selected node to treat a patient, wherein the performance feedback comprises system performance feedback indicative of power consumption of a medical device that delivers the stimulation therapy according to the stimulation parameters defined by the selected node.

18. The system of claim 17, wherein the performance feedback further comprises at least one of a beneficial effect or an adverse effect.

19. The system of claim 18, wherein the processor weights at least one of the beneficial effects, the adverse effects, and the system performance feedback to indicate a relative importance of at least two of the beneficial effects, the adverse effects, and the system performance feedback for defining the program path.

20. The system of claim 17, wherein the system performance feedback comprises a power usage value, and wherein the processor defines the program path by selecting at least one node to minimize the power usage value.

21. The system of claim 17, wherein the stimulation therapy comprises at least one of spinal cord stimulation, deep brain stimulation, peripheral nerve stimulation, or peripheral nerve field stimulation.

22. The system of claim 17, wherein the stimulation therapy treats a movement disorder.

23. The system of claim 17, wherein the processor specifies which stimulation parameters are adjusted at which levels of the tree based on user input.

24. The system of claim 17, wherein:
the processor prompts the user via the user interface to provide the performance feedback input; and
the processor receives the performance feedback input from a user via the user interface; and
the user interface displays the performance feedback input to the user.

25. The system of claim 17, further comprising a sensor that measures a physiological parameter of the patient, wherein the processor receives the performance feedback input from the sensor.

26. The system of claim 25, wherein the sensor is configured to measure at least one of a gait, a tremor, a seizure, and posture.

27. The system of claim 17, wherein the therapeutic tree comprises at least four levels.

28. The system of claim 27, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

29. The system of claim 28, wherein the first level of the tree comprises two sublevels of the tree including a first sublevel that specifies an adjustment to an electrode level of a complex electrode array geometry and a second sublevel that specifies an adjustment to an electrode perimeter position of the complex electrode array geometry.

30. The system of claim 17, wherein the stimulation parameters include stimulation electrode configuration, stimulation pulse rate, stimulation pulse width, and stimulation pulse amplitude.

31. The system of claim 17, wherein the processor resides within an external programmer associated with an implantable electrical stimulator.

32. The system of claim 17, wherein the processor:
- detects an activity undertaken by the patient;
- defines a program path specific to the activity through the tree structure along a series of the interconnected nodes for which performance feedback regarding stimulation therapy delivered according to the stimulation parameters defined by the nodes during the activity exceeds a threshold level;
- subsequently detects the activity; and
- control delivery of the stimulation therapy to the patient according to the previously defined program path specific to the activity.

33. A computer-readable medium comprising instructions that cause a processor to:
- define a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, and the nodes in different levels specify adjustments to the value of different types of stimulation parameters;
- define a program path through the tree structure along a series of the interconnected nodes for which performance feedback regarding stimulation therapy delivered according to the stimulation parameters defined by the nodes exceeds a threshold level, wherein the performance feedback comprises system performance feedback indicative of power consumption of a medical device that delivers the stimulation therapy according to the stimulation parameters defined by the selected node;
- select one of the nodes in the program path; and
- deliver the stimulation therapy to a patient based on the parameters defined by the selected node to treat a patient.

34. The computer-readable medium of claim 33, wherein the performance further comprises at least one of a beneficial effect or an adverse effect.

35. The computer-readable medium of claim 34, further comprising instructions that cause the processor to weight at least one of the beneficial effects, the adverse effects, and the system performance feedback to indicate a relative importance of at least two of the beneficial effects, the adverse effects, and the system performance feedback for defining the program path.

36. The computer-readable medium of claim 33, further comprising instructions that cause the processor to receive the performance feedback input from a sensor that measures a physiological parameter of the patient.

37. The computer-readable medium of claim 36, further comprising instructions that cause the processor receive sensor measurements of at least one of a gait, a tremor, a seizure, and posture.

38. The computer-readable medium of claim 33, wherein the therapeutic tree comprises at least four levels.

39. The computer-readable medium of claim 38, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

40. The computer-readable medium of claim 39, wherein the first level of the tree comprises two sublevels of the tree including a first sublevel that specifies an adjustment to an electrode level of a complex electrode array geometry and a second sublevel that specifies an adjustment to an electrode perimeter position of the complex electrode array geometry.

41. The computer-readable medium of claim 33, wherein the instructions cause the processor to define the tree within an external programmer associated with an implantable electrical stimulator.

42. The computer-readable medium of claim 33, wherein the stimulation therapy treats a movement disorder of the patient.

43. The computer-readable medium of claim 33, further comprising instructions that cause the processor to:
- detect an activity undertaken by the patient;
- define a program path specific to the activity through the tree structure along a series of the interconnected nodes for which performance feedback regarding stimulation therapy delivered according to the stimulation parameters defined by the nodes during the activity exceeds a threshold level;
- subsequently detect the activity; and
- control delivery of the stimulation therapy to the patient according to the previously defined program path specific to the activity.

* * * * *